United States Patent
Puder et al.

(10) Patent No.: US 10,328,045 B2
(45) Date of Patent: Jun. 25, 2019

(54) DIETARY EMULSION FORMULATIONS AND METHODS FOR USING THE SAME

(71) Applicants: CHILDREN'S MEDICAL CENTER CORPORATION, Boston, MA (US); BETH ISRAEL DEACONESS MEDICAL CENTER, INC., Boston, MA (US)

(72) Inventors: Mark Puder, Medfield, MA (US); Bruce R. Bistrian, Ipswich, MA (US)

(73) Assignees: Children's Medical Center Corporation, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 15/509,766

(22) PCT Filed: Sep. 10, 2015

(86) PCT No.: PCT/US2015/049336
§ 371 (c)(1),
(2) Date: Mar. 8, 2017

(87) PCT Pub. No.: WO2016/040570
PCT Pub. Date: Mar. 17, 2016

(65) Prior Publication Data
US 2017/0304248 A1 Oct. 26, 2017

Related U.S. Application Data

(60) Provisional application No. 62/049,672, filed on Sep. 12, 2014.

(51) Int. Cl.
| | | |
|---|---|---|
| *A61K 31/202* | (2006.01) | |
| *A61K 9/107* | (2006.01) | |
| *A61K 35/60* | (2006.01) | |
| *A61K 9/00* | (2006.01) | |
| *A61K 8/06* | (2006.01) | |
| *A61K 49/00* | (2006.01) | |
| *A61Q 19/08* | (2006.01) | |
| *A61K 8/31* | (2006.01) | |
| *A61K 8/34* | (2006.01) | |
| *A61K 8/368* | (2006.01) | |
| *A61K 8/37* | (2006.01) | |
| *A61K 8/58* | (2006.01) | |
| *A61K 8/64* | (2006.01) | |
| *A61K 8/67* | (2006.01) | |
| *A61K 8/97* | (2017.01) | |
| *A23L 33/12* | (2016.01) | |
| *A23L 33/00* | (2016.01) | |
| *A23L 29/10* | (2016.01) | |

(52) U.S. Cl.
CPC ............ *A61K 31/202* (2013.01); *A23L 29/10* (2016.08); *A23L 33/12* (2016.08); *A23L 33/30* (2016.08); *A23L 33/40* (2016.08); *A61K 8/062* (2013.01); *A61K 8/31* (2013.01); *A61K 8/342* (2013.01); *A61K 8/345* (2013.01); *A61K 8/368* (2013.01); *A61K 8/37* (2013.01); *A61K 8/585* (2013.01); *A61K 8/64* (2013.01); *A61K 8/67* (2013.01); *A61K 8/97* (2013.01); *A61K 9/0029* (2013.01); *A61K 9/107* (2013.01); *A61K 35/60* (2013.01); *A61K 49/0006* (2013.01); *A61Q 19/08* (2013.01); *A23V 2002/00* (2013.01); *A61K 2800/20* (2013.01); *A61K 2800/48* (2013.01); *A61K 2800/884* (2013.01)

(58) Field of Classification Search
CPC .... A61K 31/202; A61K 35/60; A61K 9/0029; A61K 9/107; A23L 33/40; A23L 33/12; A23L 29/10; A23L 33/30; A23V 2002/00
See application file for complete search history.

(56) References Cited

U.S. PATENT DOCUMENTS

| | | | |
|---|---|---|---|
| 7,919,526 B2 | 4/2011 | Rozen | |
| 8,106,093 B2 | 1/2012 | Roe | |
| 8,241,672 B2 | 8/2012 | Driscoll | |
| 8,652,508 B2 | 2/2014 | Puder | |

FOREIGN PATENT DOCUMENTS

| | | | |
|---|---|---|---|
| EP | 0687418 | A2 | 12/1995 |
| EP | 1279400 | A1 | 1/2003 |
| WO | 1989/002275 | A1 | 3/1989 |
| WO | 2010/104575 | A2 | 9/2010 |
| WO | 2013/063067 | A1 | 5/2013 |

OTHER PUBLICATIONS

Bach et al., "Medium-chain triglycerides: an update", Am J Clin Nutr 36(5) 950-962 (1982).
Calkins et al., "Pediatric intestinal failure-associated liver disease is reversed with 6 months of intravenous fish oil", JPEN J Parenter Enteral Nutr 38(6) 682-692 (2014).
Chang et al., "Seizure control by ketogenic diet-associated medium chain fatty acids", Neuropharmacology 69: 105-114 (2013).
Cober et al., "Intravenous fat emulsions reduction for patients with parenteral nutrition-associated liver disease", J Pediatr 160(3) 421-427 (2012).

(Continued)

*Primary Examiner* — Sarah Pihonak
*Assistant Examiner* — Jason Deck
(74) *Attorney, Agent, or Firm* — Nixon Peabody LLP

(57) ABSTRACT

Disclosed herein is a formulation that can take the form of an emulsion which contains total enteral or parenteral nutrition for a recipient subject. The formulation includes as the sole fat components: (i) medium chain triglycerides; and (ii) very long chain fatty acids selected from (a) very long chain omega-3 polyunsaturated fatty acids; and (b) docosahexaenoic acid and arachidonic acid in a ratio of about 10:1 (v/v or w/w) to about 2000:1 (v/v or w/w). The sole fat components provide about 10% to about 90% total calories of the formulation, and the medium chain triglycerides provide about 25%-95% total fat calories of the formulation. Methods and kits for utilizing the formulation and for treating various disorders and diseases that involve an inflammatory response are also disclosed.

12 Claims, 6 Drawing Sheets

(56) References Cited

OTHER PUBLICATIONS

Colomb et al., "Role of Lipid Emulsions in Cholestasis Associated with Long-Term Parenteral Nutrition in Children", JPEN 24(6) 345-350 (2000).
Cook et al., "Elevated thromboxane levels in the rat during endotoxic shock: protective effects of imidazole, 13-azaprostanoic acid, or essential fatty acid deficiency", J Clin Invest 65(1) 227-230 (1980).
Endres et al., "The effect of dietary supplementation with n-3 polyunsaturated fatty acids on the synthesis of interleukin-1 and tumor necrosis factor by mononuclear cells", N Engl J Meed 320(5) 265-271 (1989).
Guglielmi et al., "Catheter-related complications in long-term home parenteral nutrition patients with chronic intestinal failure", J Vasc Access 13(4) 490-497 (2012).
Hansen et al., "Role of Linoleic Acids in Infant Nutrition", Pediatrics 31(1) 171-192 (1963).
Kono et al., "Enteral diets enriched with medium-chain triglycerides and N-3 fatty acids prevent chemically induced experimental colitis in rats", Transl Res 156(5) 282-291 (2010).
Kono et al., "Medium-chain triglycerides enhance secretory IgA expression in rat intestine after administration of endotoxin", Am J Physiol Gastrointest Liver Physiol 286(6) G1081-G1089 (2004).
Kono et al., "Medium-chain triglycerides inhibit free radical formation and TNF-α production in rats given enteral ethanol", American Physiological Society 278(3) G467-G476 (2000).
Kono et al., "Protective effects of medium-chain triglycerides on the liver and gut in rats administered endotoxin", Ann Surg 237(2) 246-255 (2003).
Kurvinen et al., "Parenteral plant sterols and intestinal failure-associated liver disease in neonates", J Pediatr Gastroenterol Nutr 54(6) 803-811 (2012).
Le et al., "Docosahexaenoic acid and arachidonic acid prevent essential fatty acid deficiency and hepatic steatosis", JPEN J Parenter Enteral Nutr 36(4) 431-441 (2012).
Le et al., "Parenteral fish oil as monotherapy improves lipid profiles in children with parenteral nutrition-associated liver disease", JPEN Jparenter Enteral Nutr 34(5) 477-484 (2010).
Le et al., "The essentiality of arachidonic acid and docosahexaenoic acid", Prostaglandins Leukot Essent Fatty Acids 31(2-3) 165-170 (2009).
Ling et al., "Arachidonic acid and docosahexaenoic acid supplemented to an essential fatty acid-deficient diet alters the response to endotoxin in rats", Metabolism 61(3) 395-406 (2012).
Ling et al., "Effects of glucose or fat calories in total parenteral nutrition on fat metabolism and systemic inflammation in rats", Metabolism 60(2) 195-205 (2011).
Ling et al., "Purified fish oil eliminating linoleic and alpha linolenic acid meets essential fatty acid requirements in rats", Metabolosim 61(10) 1443-1451 (2012).
Ling et al., "Role of arachidonic acid in the regulation of the inflammatory response in TNF-alpha-treated rats", JPEN J Parenter Enteral Nutr 22(5) 268-275 (1998).
Mascioli et al., "Enhanced survival to endotoxin in guinea pigs fed IV fish oil emulsion", Lipids 23(6) 623-625 (1988).
Merritt, "Cholestasis associated with total parenteral nutrition", Journal of Pediatric Gastroenterology and Nutrition 5(1) 9-22 (1986).
Murphy et al., "Low dose supplementation with two different marine oils does not reduce pro-inflammatory eicosanoids and cytokines in vivo", Asia Pac J Clin Nutr 15(3) 418-424 (2006).
Nanji et al., "Dietary saturated fatty acids reverse inflammatory and fibrotic changes in rat liver despite continued ethanol administration", J Pharmacol Exp Ther 299(2) 638-644 (2001).
Nehra et al., "Prolonging the female reproductive lifespan and improving egg quality with dietary omega-3 fatty acids", Aging Cell 11(6) 1046-1054 (2012).
Nehra et al., "Provision of a soy-based intravenous lipid emulsion at 1 g/kg/d does not prevent cholestasis in neonates", JPEN J Parenter Enteral Nutr 37(4) 498-505 (2013).
Palombo et al., "Effect of short-term enteral feeding with eicosapentaenoic and gamma-linolenic acids on alveolar macrophage eicosanoid synthesis and bactericidal function in rats", Crit Care Med 27(9) 1908-1915 (1999).
Pironi et al., "Long-term follow-up of patients on home parenteral nutrition in Europe: implications for intestinal transplantation", Gut 60(1) 17-25 (2011).
Pomposelli et al., "Attenuation of the febrile response in guinea pigs by fish oil enriched diets", JPEN J Parenter Enteral Nutr 13(2) 136-140 (1989).
Premkumar et al., "High rates of resolution of cholestasis in parenteral nutrition-associated liver disease with fish oil-based lipid emulsion monotherapy", J Pediatr 162(4) 793-798 (2013).
Puder et al., "Parenteral fish oil improves outcomes in patients with parenteral nutrition-associated liver injury", Ann Aurg 250(3) 395-402 (2009).
Reger et al., "Effects of beta-hydroxybutyrate on cognition in memory-impaired adults", Neurobiol Aging 25(3) 311-314 (2004).
Ronis et al., "Dietary saturated fat reduces alcoholic hepatotoxicity in rats by altering fatty acid metabolism and membrane composition", J Nutr 134(4) 904-912 (2004).
Rouis et al., "Therapeutic response to medium-chain triglycerides and omega-3 fatty acids in a patient with the familial chylomicronemia syndrome", Arterioscler Thromb Vasc Biol 17(7) 1400-1406 (1997).
Sanchez et al., "The effect of lipid restriction on the prevention of parenteral nutrition-associated cholestasis in surgical infants", J Pediatr Surg 48(3) 573-578 (2013).
Sanders et al., "Septic complications of total parenteral nutrition. A five year experience.", Am J Surg 132(2) 214-220 (1976).
Shi et al., "TLR4 links innate immunity and fatty acid-induced insulin resistance", J Clin Invest 116(11) 3015-3025 (2006).
Sierra et al., "Fish oil feeding improves muscle glucose uptake in tumor necrosis factor-treated rats", Metabolism 44 (10) 1356-1370 (1995).
Squires et al., "Natural history of pediatric intestinal failure: initial report from the Pediatric Intestinal Failure Consortium", J Pediatr 161(4) 723-728 (2012).
Strijbosch et al., "Fish oil prevents essential fatty acid deficiency and enhances growth: clinical and biochemical implications", Metabolism 57(5) 698-707 (2008).
Wan et al., "Invited comment: lipids and the development of immune dysfunction and infection", JPEN J Parenter Enteral Nutr 12(6 Suppl) 43S-52S (1988).
Zulyniak et al., "Fish oil supplementation alters circulating eicosanoid concentrations in young healthy men", Metabolism 62(8) 1107-1113 (2013).

DIETARY EMULSION FORMULATIONS AND METHODS FOR USING THE SAME

CROSS-REFERENCE TO RELATED APPLICATIONS

This application is a 35 U.S.C. § 371 National Phase Entry Application of International Application No. PCT/US2015/049336 filed Sep. 10, 2015, which designates the U.S., and which claims benefit under 35 U.S.C. § 119(e) of the U.S. Provisional Application No. 62/049,672 filed Sep. 12, 2014, the contents of each of which are incorporated herein by reference in their entirety.

GOVERNMENT SUPPORT

This invention was made with Government Support under Contract Nos. F532 HD 071715-02, 2T32DK007754-14, 5 T32 HD007466-16, and 5 T32 HD007466-17, all awarded by the National Institutes of Health. The government has certain rights in the invention.

TECHNICAL DISCLOSURE

Embodiments of various aspects described herein relate to dietary emulsion formulations for total enteral or parenteral nutrition as well as methods of using the same for prevention of systemic inflammatory responses.

BACKGROUND

Essential fatty acids (EFAs), necessary for growth, development, and a variety of biological functions, must be provided by the diet. Historically, polyunsaturated fatty acids (PUFA) alpha linolenic acid (ALA, n-3 PUFA) and linoleic acid (LA, n-6 PUFA) have been considered the two essential fatty acids. However, recent reports have shown that the downstream metabolic products of ALA and LA, docosahexaenoic acid (DHA) and arachidonic acid (ARA), respectively, are sufficient to sustain growth, development and reproductive function (Le et al., Prostaglandins, leukotrienes, and essential fatty acids. 2009; 81(2-3):165-170; Ling et al., Metabolism: clinical and experimental, 2012; 61(10):1443-1451; and Nehra et al., Aging cell. 2012; 11(6): 1046-1054).

For individuals dependent on parenteral nutrition (PN), EFAs must be provided intravenously as a lipid emulsion. Commercially available lipid formulations in the United States have been exclusively soybean oil-based and contain high levels of LA and lower levels of ALA. Soybean oil-based lipid emulsions are implicated in the development of parenteral nutrition-associated liver disease (PNALD), a progressive and often lethal complication affecting up to 74% of patients dependent on long-term PN (Colomb et al., JPEN Journal of parenteral and enteral nutrition. 2000; 24(6):345-350; Kurvinen et al., Journal of pediatric gastroenterology and nutrition. 2012; 54(6):803-811; Merritt. Journal of pediatric gastroenterology and nutrition. 1986; 5(1):9-22; Squires et al. The Journal of pediatrics. 2012; 161(4):723-728 e722).

The reduction of the total lipid dose of soybean-based lipid emulsions from 2-3 g/kg/day to 1 g/kg/day has been discussed in some previous reports to decrease the risk of development of PNALD (Cober et al. The Journal of pediatrics. 2012; 160(3):421-427; Sanchez et al. Journal of pediatric surgery. 2013; 48(3):573-578). However, these reports were not supported by Nehra et al., who demonstrated that a lipid-restrictive practice does not prevent cholestasis or PNALD (JPEN Journal of parenteral and enteral nutrition. 2013; 37(4):498-505). Alternative lipid sources have been previously discussed as another potential strategy to prevent liver disease in PN-dependent individuals. For example, a fish oil-based lipid emulsion, provided at 1 g/kg/day, has been discussed to reverse the progression toward liver failure in patients with PNALD (Calkins et al., JPEN Journal of parenteral and enteral nutrition. 2013; 38(6): 682-692; Premkumar et al. The Journal of pediatrics. 2013; 162(4):793-798 e791; and Puder et al. Annals of surgery. 2009; 250(3):395-402). Additionally, fish oil has been previously discussed to prevent essential fatty acid deficiency and enhance growth (Strijbosch et al., Metabolism, 2008, 57: 698-707). However, PN formulations provided with low doses of lipids necessitate higher calories from carbohydrates (e.g., dextrose) in order to meet the daily caloric needs of the PN-dependent individual, a consideration that is especially important in developing infants and children. PN formulations high in dextrose predispose patients to hyperglycemia and increased central venous catheter infections, hepatic steatosis, and glycosuria, complications that can lead to significant morbidity and mortality in an already-fragile population (Guglielmi et al. The journal of vascular access. 2012, 13(4):490-497; Pironi et al. Gut. 2011, 60(1):17-25; Sanders et al. American journal of surgery. 1976; 132(2):214-220).

Recently, non-essential fatty acids, so called "EFA-free" lipids, have been discussed to be utilized as additives to lipid emulsions in order to augment the total fat calories provided and decrease the requirement for additional dextrose in PN. Ling et al. discussed the metabolic effects of combinations of EFAs with hydrogenated coconut oil (HCO), an EFA-free lipid source and reported that rats fed a diet with HCO as the sole source of calories showing lower inflammatory response after an endotoxin challenge, as measured by serum IL-6 and C-reactive protein, when compared to rats fed HCO supplemented with DHA and ARA (Metabolism: clinical and experimental, 2012; 61(3):395-406). Cook et al reported a decreased systemic inflammatory response in states of essential fatty acid deficiency in rats (The Journal of clinical investigation. 1980; 65(1):227-230).

Medium-chain triglycerides (MCT) oil has been previously discussed to prevent alcohol-induced liver injury in animal models (Kono et al., American journal of physiology. Gastrointestinal and liver physiology. 2000, 278(3):G467-476; Nanji et al., The Journal of pharmacology and experimental therapeutics. 2001, 299(2):638-644; Ronis et al., The Journal of nutrition. 2004; 134(4):904-912). Other previous reports have discussed that dietary supplementation of MCT can reduce the degree of endotoxin-induced intestinal and hepatic injury in rats (Kono et al., American journal of physiology. Gastrointestinal and liver physiology. 2004, 286(6):G1081-1089; and Kono et al., Annals of surgery. 2003; 237(2):246-255). MCT were also discussed for several potential therapeutic applications including inflammatory bowel disease and, in combination with a ketogenic diet, neurological conditions such as Alzheimer's disease and epilepsy (Chang et al., Neuropharmacology. 2013; 69:105-114; Kono et al., Translational research: the journal of laboratory and clinical medicine. 2010; 156(5):282-291; Reger et al. Neurobiology of aging. 2004; 25(3):311-314).

In 2012, the American Society of Parenteral and Enteral Nutrition discussed alternatives oil-based fat emulsions other than soybean-oil based fat emulsion and suggested further research is required to identify optimum intravenous fat emulsions for specific patient populations in a compromised state. Vanek et al., Nutrition in clinical practice: Official publication of the American Society for Parenteral and Enteral Nutrition, 2012, 27:150-192. Accordingly, there is a need for development of an optimized lipid formulation, which provides sufficient EFAs to sustain growth and development, while modifying the intensity of inflammation. These lipid formulations should be of high value to the PN-dependent population.

SUMMARY

Standard fish oil preparations (e.g., native fish oil or unpurified fish oil) have been previously shown to be anti-inflammatory. Aspects of the invention stem from the discovery that long term administration of very long chain fatty acids (i.e., fatty acids having a carbon length greater than 18) as the sole fat component for total nutrition (e.g., to prevent essential fatty acid deficiency) increases the intensity of systemic inflammation (e.g., in response to endotoxin). Other aspects of the invention relate to the unexpected finding that addition of medium chain triglycerides (MCT) to this diet decreases a subject's propensity for developing a systemic inflammatory response. In particular, long-term nutrition diet with either purified fish oil (having high levels of very long chain omega-3 polyunsaturated fatty acids (VLC omega-3 PUFAs), including, e.g., eicosapentaenoic acid (EPA) and docosahexaenoic acid (DHA), and considerably low level of arachidonic acid (ARA), or only two active components (DHA and ARA) as the sole fat components in a diet increases the systemic inflammatory response arising from a challenge (e.g., with endotoxin). However, provision of MCT instead of hydrogenated coconut oil (no essential fatty acids) reduces the severity of essential fatty acid deficiency over time, and addition of MCT (e.g., from fractionalizaton of tropical oils such as palm kernel oil, coconut oil, babassu oil, etc.) to the purified fish oil mitigates the systemic inflammatory response induced by long term administration of the purified fish oil alone. Further, the addition of MCT to purified fish oil also allows the provision of substantial fat calories, which in turn allows the reduction of the carbohydrate portion of the diet. This results in a more desirable fat:carbohydrate ratio for long term nutrition treatment. Accordingly, aspects of the invention relate to a formulation (e.g., as an emulsion) for total enteral or parenteral nutrition of a human subject, the components of which are based on these findings. Other aspects of the invention relate to administration of the emulsion formulation to provide total enteral or parenteral nutrition to a human subject in need thereof. Administration of the formulation described herein can simultaneously prevent essential fatty acid deficiency, reduce the risk of parenteral nutrition associated liver disease, and decrease development of a systemic inflammatory response in a recipient subject.

One aspect of the invention relates to an emulsion formulation for total enteral or parenteral nutrition of a human subject (e.g., daily nutrition). The emulsion formulation comprises as the sole fat components: (i) medium chain triglycerides; and (ii) very long chain fatty acids selected from (a) very long chain omega-3 polyunsaturated fatty acids (VLC omega-3 PUFAs); and (b) docosahexaenoic acid (DHA) and arachidonic acid (AA) in a ratio of about 10:1 (v/v or w/w) to about 2000:1 (v/v or w/w). The sole fat components provide about 10% to about 90% total calories of the formulation (e.g., based on daily calories of a recipient subject), and the medium chain triglycerides provide about 25%-95% total fat calories.

The emulsion formulation described herein can have varying amounts of the fat components, the amount of which are determined in order to suit the needs of the subject. In one embodiment of the formulation described herein, the sole fat components are present in an amount of about 10 g to about 50 g per 100 mL of the formulation. In one embodiment, the sole fat components are present in an amount of about 20 g to about 30 g per 100 mL of the formulation. In one embodiment, the total calories of the formulation can vary from about 1000 kcal/kg of the formulation to about 4000 kcal/kg of the formulation. In one embodiment, the very long chain fatty acids can provide about 3% total calories of the formulation.

The medium chain triglycerides used in the emulsion formulation described herein can have fatty acid chains with a carbon length of 6, 8, and/or 10. In one embodiment, the medium chain triglycerides and the very long chain fatty acids can be present in a weight ratio of at least about 1:1 or higher. In one embodiment, the weight ratio of the medium chain triglycerides and the very long chain fatty acids is about 50:50. In some embodiments, the weight ratio of the medium chain triglycerides to the very long chain fatty acids is about 70:30.

In one embodiment, the very long chain fatty acids are VLC omega-3 PUFAs. Accordingly, in one embodiment, the emulsion formulation comprises as the sole fat components: (i) medium chain triglycerides; and (ii) very long chain omega-3 polyunsaturated fatty acids (VLC omega-3 PUFAs), wherein the sole fat components provide about 10% to about 90% total calories of the formulation, and the medium chain triglycerides provide about 25%-95% total fat calories. The VLC omega-3 PUFAs can be selected from the group consisting of docosahexaenoic acid (DHA), eicosapentaenoic acid (EPA), eicosatrienoic (stearidonic) acid, and 5-docosapentaenoic acid (DPA), and combinations thereof.

In one embodiment, the very long chain fatty acids are DHA and AA. Accordingly, in one embodiment, the emulsion formulation comprises as the sole fat components: (i) medium chain triglycerides; and (ii) docosahexaenoic acid (DHA) and arachidonic acid (AA) in a ratio of about 10:1 (v/v or w/w) to about 2000:1 (v/v or w/w), wherein the sole fat components provide about 10% to about 90% total calories of the formulation, and the medium chain triglycerides provide about 25%-95% total fat calories. In some embodiments, the ratio of DHA and AA is about 20:1 (v/v or w/w).

Another aspect described herein is directed to a method of providing total enteral or parenteral nutrition to a subject in need thereof that minimizes the subject's propensity for developing a systemic inflammatory response. The method consists essentially of administration of any embodiment of the emulsion formulation described herein every 24 hours.

The daily amount of the emulsion formulation administered to a subject in need depends on, e.g., daily energy expenditure of the subject, and the total calories per unit weight of the formulation. The subject can be given the daily amount of the emulsion formulation in a single dose or in separate doses.

The administration of the emulsion formulation can be performed for any duration of time (e.g., short-term, long term, or even permanent) according to the needs of a subject recipient. In one embodiment, the administration is performed for at least 1 week or longer. In one embodiment, the administration is performed for at least 1 month or longer. In one embodiment, the administration is performed for at least 3 months or longer. In one embodiment, the administration is performed for at least 6 months or longer. In one embodiment, the administration is performed for at least 1 year or longer.

Subjects (e.g., human) of any age (e.g., infants, children, adults, and elderly) who are susceptible to a systemic inflammatory response can be administered the emulsion formulation described herein as total parenteral or enteral nutrition. In one embodiment, the subject is a subject who is being administered purified fish oil for total parenteral or enteral nutrition. In one embodiment, the subject has essential fatty acid deficiency. In one embodiment, the subject has an intestinal failure. In one embodiment, the subject has a parenteral nutrition associated liver disease. In one embodiment, the subject has fatty liver disease. In one embodiment, the subject has hypertriglyceridemia. In one embodiment, the subject has traumatic brain injury. In one embodiment, the subject is a pregnant woman. In one embodiment, the subject has or be likely to develop an inflammatory disease or disorder.

Accordingly, methods for treatment and/or prevention of a condition likely resulting in a systemic inflammatory response are also encompassed by the invention. For example, in one aspect, the invention relates to a method for treating essential fatty acid deficiency. The method for treating essential fatty acid deficiency consists essentially of administration of the emulsion formulation every 24 hours. The administration can be performed enterally or parenterally (e.g., by intravenous methods).

Another aspect of the invention relates to a method for providing nutrition to a subject with an intestinal failure. The method consists essentially of parenteral administration of the emulsion formulation described herein for total daily nutrition.

Another aspect of the invention relates to a method for treating a subject prior to, and/or following, a surgical procedure. The method involves parenteral or enteral administration of the emulsion formulation described herein for total daily nutrition of the subject.

BRIEF DESCRIPTION OF THE DRAWINGS

FIG. 2A shows the trajectory for each animal over time for HCO-treated group.

FIG. 2B shows the trajectory for each animal over time for MCT-treated group. FIG. 2C shows the aggregated results by HCO or MCT diet (mean and 95% confidence interval from a generalized linear model). The week-by-diet interaction is statistically significant (P=0.003). At 12 weeks, HCO-fed animals showed increased triene:tetraene ratios relative to MCT-fed animals, indicating a slightly greater degree of essential fatty acid deficiency (EFAD) in the HCO group.

DETAILED DESCRIPTION OF THE INVENTION

Figure 1:
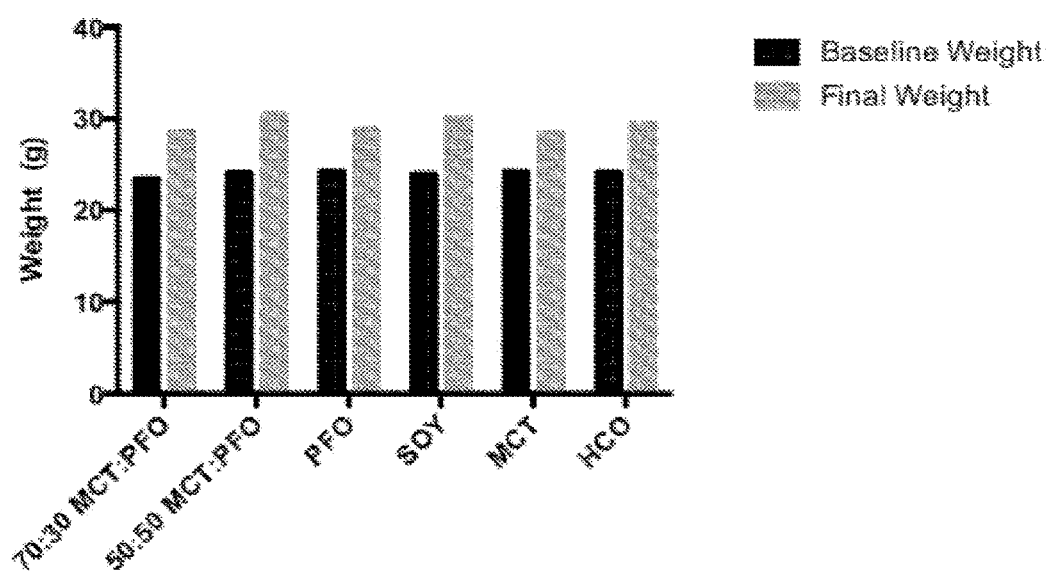
FIG. 1 is a bar graph showing animal weight by treatment group. All groups gained weight during the treatment period. There were no significant weight differences between treatment groups at the beginning or the end of treatment.

Aspects of the invention stem from the discovery that long term administration of very long chain fatty acids (i.e., fatty acids having a carbon length greater than 18) as the sole fat component for total nutrition (e.g., to prevent essential fatty acid deficiency) increases the intensity of systemic inflammation (e.g., in response to endotoxin). Aspects of the invention also relate to the unexpected finding that addition of medium chain triglycerides (MCT) to very long chain fatty acids decreases a subject's propensity for developing a systemic inflammatory response.

While standard fish oil preparations (e.g., native fish oil or unpurified fish oil) have been previously shown to be anti-inflammatory, long-term nutrition treatment with either purified fish oil (having high levels of very long chain omega-3 polyunsaturated fatty acids (VLC omega-3 PUFAs), including, e.g., eicosapentaenoic acid (EPA) and docosahexaenoic acid (DHA), and considerably low level of arachidonic acid (ARA)) or only two active components (DHA and ARA) as the sole fat components in a diet will increase the systemic inflammatory response after an endotoxin challenge. However, provision of MCT instead of hydrogenated coconut oil (no essential fatty acids) reduces the severity of essential fatty acid deficiency over time, and addition of MCT (e.g., from fractionalizaton of tropical oils such as palm kernel oil, coconut oil, babassu oil, etc.) to the purified fish oil mitigates the systemic inflammatory response induced by long term administration of the purified fish oil alone. Further, when fish oil is used alone, fat is only provided in limited amounts and thus carbohydrate calories are generally used to provide the energy gap to meet energy requirement. Glucose calories in total parenteral nutrition or glucose or oligosaccharides in enteral nutrition in the critically ill subject population increase the risk of hyperglycemia and de novo lipogenesis because of increased glucose production and insulin resistance characteristic of the systemic inflammatory response (Ling et al., Metabolism, 2011, 60: 195-205). In accordance with various aspects described herein, the addition of MCT to purified fish oil also allows the provision of substantial fat calories to reduce the carbohydrate burden, thus providing a more desirable fat:carbohydrate ratio for long term nutrition treatment. Accordingly, aspects of the invention relate to formulations (e.g., as emulsions) for total enteral or parenteral nutrition of a human subject based on these findings and methods of providing total enteral or parenteral nutrition to a human subject in need thereof.

Emulsion formulations comprising MCTs and very long chain fatty acids

One aspect of the invention relates to an emulsion formulation for total nutrition (e.g., total daily nutrition) of a subject (e.g., a human subject) for enteral or parenteral administration. The emulsion formulation includes as fat components: (i) medium chain triglycerides; and (ii) very long chain fatty acids selected from (a) very long chain omega-3 polyunsaturated fatty acids (VLC omega-3 PUFAs); and (b) docosahexaenoic acid (DHA) and arachidonic acid (AA) in a ratio of about 10:1 (v/v or w/w) to about 2000:1 (v/v or w/w). The sole fat components provide about 10% to about 90% total calories of the formulation (e.g., based on daily calories of a recipient subject), and wherein the medium chain triglycerides provide about 25%-95% total fat calories.

In one embodiment, the sole fat components provide about 20% to about 80%, or about 30% to about 70%, or about 40% to about 60%, or about 20% to about 90%, or about 30% to about 90%, or about 40% to about 90%, or about 50% to about 90%, or about 60% to about 90%, or about 10% to about 80%, or about 10% to about 70%, or about 10% to about 60%, or about 10% to about 50%, or about 10% to about 40%, or about 10% to about 30% total calories of the formulation.

As used herein, the term "medium chain triglycerides" refers to a molecule comprising a glycerol molecule that is ester-linked to three saturated fatty acid molecules. Each saturated fatty acid molecule in the context of the medium chain triglycerides has 6-12 carbons; these are considered to be medium chain fatty acids. While long-chain saturated fatty acids are generally considered to have pro-inflammatory effects (Shi et al., J. Clin. Invest., 2006, 116: 3015-3125), medium chain saturated fatty acids can be anti-inflammatory (Kono et al., Ann Surg, 2003, 237: 246-255). The saturated fatty acid molecules in the context of the medium chain triglycerides are one or more of a C6 fatty acid (e.g., caproic acid), a C8 fatty acid (caprylic acid), a C10 fatty acid (e.g., capric acid), and a C12 fatty acid (e.g., lauric acid). In one embodiment, the medium chain triglycerides used in the emulsion formulation described herein have saturated fatty acid molecules with a carbon length of 6, 8, 10, 12, and combinations thereof. In one embodiment, the medium chain triglycerides used in the emulsion formulation described herein have saturated fatty acid molecules with a carbon length of 6, 8, 10, and combinations thereof (e.g., combination of 6 and 8; combination of 6 and 10, combination of 8 and 10, and combination of 6, 8, and 10). In one embodiment, all the medium chain triglycerides in the emulsion formulation described herein have saturated fatty acid molecules with a carbon length of 6. In one embodiment, all the medium chain triglycerides in the emulsion formulation described herein have saturated fatty acid molecules with a carbon length of 8. In one embodiment, all the medium chain triglycerides in the emulsion formulation described herein have saturated fatty acid molecules with a carbon length of 10. The medium chain triglycerides can be obtained from various sources such as fractionation of plant or tropical plant oils, including, e.g., but not limited to coconut oil, palm kernel oil, babassu oil, and combinations thereof.

In one embodiment, the medium chain triglycerides are made up of a mixture of C6 (1-2%), C8 (65-75%), C10 (25-35%), and C12 (1-2%) saturated fatty acids. See Bach and Babayan, The American Journal of Clinical Nutrition (1982) 36: 950-962. In one embodiment, the medium chain triglycerides are made up of a mixture of C6 (0-2%), C8 (65-75%), C10 (25-35%), and C12 (0-2%) saturated fatty acids. In one embodiment, the medium chain triglycerides are made up of a mixture of C8 (67%) and C10 (33%) saturated fatty acids.

Medium chain triglycerides are available commercially, for example, obtained from Mead Johnson Nutrition, Stepan, or Health and Sport LLC.

In one embodiment, at least about 1% or more (including, e.g., at least about 5%, at least about 10%, at least about 20%, at least about 30%, at least about 40%, at least about 50%, at least about 60%, at least about 70%, at least about 80%, at least about 90%, at least about 95%, at least about 98% or up to 100%) of the medium chain triglycerides present in the emulsion formulation described herein can be replaced by medium chain fatty acids. The term "medium chain fatty acid" as used herein refers to a carboxylic acid with a saturated aliphatic tail (chain) having 6-12 carbons. Examples of medium chain fatty acids include, but are not limited to, a C6 fatty acid (e.g., caproic acid), a C8 fatty acid (caprylic acid), a C10 fatty acid (e.g., capric acid), a C12 fatty acid (e.g., lauric acid), and any combinations thereof. In some embodiments, the medium chain fatty acids used in the emulsion formulation described herein can have a carbon length of 6, 8, 10, and combinations thereof.

In one embodiment, the medium chain triglycerides provide about 25%-95% total fat calories. In one embodiment, the medium chain triglycerides provide about 30%-90%, or about 40%-80%, or about 50%-70%, or about 30%-95%, or about 40%-95%, or about 50%-95%, or about 60%-95%, or about 70%-95%, or about 80%-95% total fat calories of the formulation. As used herein, the term "total fat calories" refers to total calories of the sole fat components described herein, i.e., medium chain triglycerides and the very long chain fatty acids.

Accordingly, once the amount of medium chain triglycerides (by calories) is determined, one of skill in the art can determine the amount of very long chain fatty acids in the emulsion formulation described herein accordingly. By way of example only, in one embodiment, when the medium chain triglycerides is present in an amount that provides about 55% total fat calories, very long chain fatty acids will be present in an amount sufficient to provide the remaining 45% total fat calories.

Similarly, once the amount of very long chain fatty acids (by calories) is determined, one of skill in the art can determine the amount of medium chain triglycerides in the emulsion formulation described herein accordingly. In some embodiments, the very long chain fatty acids can provide about 5%-75% total fat calories. In some embodiments, the very long chain fatty acids present in the emulsion formulation described herein can provide about 10%-70%, or about 20%-60%, or about 30%-50%, or about 5%-60%, or about 5%-50%, or about 5%-40%, or about 5%-30%, or about 5%-20% total fat calories.

In one embodiment, the calorie ratio of the medium chain triglycerides to the very long chain fatty acids is about 35:65. This approximately corresponds to the 50:50 by weight of the medium chain triglycerides to the very long chain fatty acids. Given the calorie ratio of the medium chain triglycerides to the very long chain fatty acids, the skilled artisan can determine the weight ratio of the medium chain triglycerides to the very long chain fatty acids accordingly.

In some embodiments, the very long chain fatty acids can provide about 0.05%-70% total calories of the formulation, including, e.g., about 0.1%-65%, about 0.5%-60%, about 1%-50%, about 2%-40%, about 3%-30% total calories of the formulation. In some embodiments, the very long chain fatty acids can provide about 3% total calories of the formulation.

In some embodiments, the medium chain triglycerides and the very long chain fatty acids are present in a weight ratio of at least about 1:1 or higher. For examples, in some embodiments, the medium chain triglycerides and the very long chain fatty acids can be present in a weight ratio of at least about 1:1, at least about 3:2, at least about 2:1, at least about 5:2, at least about 3:1 or higher. In some embodiments, the weight ratio of the medium chain triglycerides and the very long chain fatty acids can be about 50:50. In some embodiments, the weight ratio of the medium chain triglycerides and the very long chain fatty acids can be about 70:30.

As used herein, the term "very long chain fatty acid" refers to a carboxylic acid with a long aliphatic tail (chain) having a length of greater than 18 carbons. For example, the very long chain fatty acids are generally selected from the fatty acids with 20 carbon length or longer, including, e.g., 22 carbon length or longer, and do not include 18-carbon fatty acids, including e.g., linoleic acid, alpha-linolenic acid, octadecatetraenoic acid, and gamma-linolenic acid. The aliphatic tail (chain) is either saturated or unsaturated. The very long chain fatty acids are selected from (a) very long chain omega-3 polyunsaturated fatty acids (VLC omega-3 PUFAs); and (b) docosahexaenoic acid (DHA) and arachidonic acid (AA) in a ratio of about 10:1 (v/v or w/w) to about 2000:1 (v/v or w/w).

In some embodiments, the very long chain fatty acids are VLC omega-3 PUFAs. Thus, one aspect provides an emulsion formulation comprising as the sole fat components, medium chain triglycerides and VLC omega-3 PUFAs, wherein the sole fat components provide about 10% to about 90% total calories of the formulation, and wherein the medium chain triglycerides provides about 25%-95% total fat calories. Exemplary VLC omega-3 PUFAs include, but are not limited to, docosahexaenoic acid (DHA), eicosapentaenoic acid (EPA), eicosatrienoic (stearidonic) acid, and 5-docosapentaenoic acid (DPA), and combinations thereof. In one embodiment, DHA alone is used. In another embodiment, EPA alone is used. Alternatively, combinations of EPA and DHA are used.

In some embodiments, the very long chain fatty acids are DHA and AA in a ratio of about 10:1 (v/v or w/w) to about 2000:1 (v/v or w/w). Accordingly, in one aspect, an emulsion formulation comprising as the sole fat components: (i) medium chain triglycerides; and (ii) docosahexaenoic acid (DHA) and arachidonic acid (AA) in a ratio of about 10:1 (v/v or w/w) to about 2000:1 (v/v or w/w), is also provided herein. The sole fat components provide about 10% to about 90% total calories of the formulation, and wherein the medium chain triglycerides provides about 25%-95% total fat calories.

In some embodiments of this aspect and other aspects described herein, the ratio of DHA to AA is about 15:1, about 20:1, about 30:1, about 40:1, about 50:1, about 100:1, about 200:1, about 300:1, about 400:1, about 500:1, about 600:1, about 700:1, about 800:1, about 900:1, about 1000:1, about 1500:1, or about 2000:1 (v/v or w/w). In some embodiments, the ratio of DHA to AA is about 20:1 (v/v or w/w). For example, in some embodiments, the very long chain fatty acids can consist essentially of or consist of: (i) about 90% to about 99.95% (w/w or v/v) docosahexaenoic acid (DHA); and about 0.05% to about 10% (w/w or v/v) arachidonic acid (AA). In some embodiments, the very long chain fatty acids can consist essentially of or consist of: (i) about 95% to about 99.95% (w/w or v/v) docosahexaenoic acid (DHA); and about 0.05% to about 50% (w/w or v/v) arachidonic acid (AA). In some embodiments, the very long chain fatty acids can consist essentially of or consist of: (i) about 99% to about 99.95% (w/w or v/v) docosahexaenoic acid (DHA); and about 0.05% to about 1% (w/w or v/v) arachidonic acid (AA).

In some embodiments, the ratio of DHA to AA is about the same as in fish oil from cold water fish. Examples of cold water fish include, but are not limited to, salmon, herring, sardines, halibut, bluefish, tuna, cod, flounder, trout, shrimp, mackerel, anchovy, and any combinations thereof.

Arachidonic acid (AA) is a polyunsaturated omega-6 fatty acid that is present in the phospholipids (especially phosphatidylethanolamine, phosphatidylcholine and phosphatidylinositides) of membranes of the body's cells, and is abundant in the brain. It is also involved in cellular signaling as a second messenger. It is also the precursor of eicosanoids, a family of other molecules with specific important roles in the body. It can be generated in the body from linoleic acid. In some embodiments, the emulsion formulation provides the minimal amount of arachidonic acid necessary and sufficient to fulfill the membrane requirements of a recipient individual. This can be accomplished, for example, by maintaining enough arachidonic acid to keep the triene/tetraene ratio <0.2. In order to accomplish this preferred ratio, the formulation can also be manipulated to lower levels of the triene mead acid.

Sources for the very long chain fatty acids include, but are not limited to, plant oils (including, e.g., canola oil, flaxseed, flaxseed oil, walnuts, leafy green vegetables, and combinations thereof), marine plankton, fungal oils, fish oils, and purified fish oils. Suitable fish oils or purified fish oils include, but are not limited to cod, menhaden, herring, mackerel, caplin, tilapia, tuna, sardine, pacific saury, krill, salmon, and the like. The sources for the very long chain fatty acids can be naturally occurring or genetically modified. As used herein, the term "purified fish oil" refers to fish oil in which saturated fat and fats with carbon lengths less than 18 were removed. Purified fish oil is a rich source of DHA and ARA that meets essential fatty acid requirements in rodent models and in humans. See, e.g., Ling et al., Metabolim: clinical and experimental, 2012, 61: 1443-1451; Le et al., JPEN. Journal of parenteral and enteral nutrition, 2012, 36: 431-441; Le et al., JPEN. Journal of parenteral and enteral nutrition, 2010, 34: 477-484; and Nehra et al., JPEN. Journal of parenteral and enteral nutrition, 2013, 37(4):498-505. Purified fish oil is available commercially, for example, obtained from Pronova BioPharma/BASF (Lysaker, Norway). Arachidonic acid is commercially available from Martek, Inc. as a fungal derivative which contains 50% arachidonic acid. In accordance with various aspects described herein, soybean oil is not used in the emulsion formulation as a source of very long chain fatty acids.

When appropriately administered to an individual, the emulsion formulation described herein is especially useful in reducing a recipient subject's propensity for developing a systemic inflammatory response. In one embodiment, emulsion formulation described herein provides the desired level of restricted omega-3 and omega-6 fatty acid to a subject by having as its contents VLC omega-3 PUFAs as the only omega-3 in the formulation, and by having as its contents arachidonic acid as the only omega-6 source in the formulation. In one embodiment, the emulsion formulation is used as the only source of fatty acids for the recipient subject.

One important function of the emulsion formulation described herein is to provide for very long chain fatty acids and MCT delivery to an individual for long term total nutrition without increasing the individual's propensity for developing a systemic inflammatory response. As such, the term "consisting essentially of" or "consists essentially of" as used herein to describe the contents of a formulation, refers to the absence of other, non-specified ingredients that either are omega-3 or omega-6 fatty acids, and/or can be metabolized into omega-3 and/or omega-6 fatty acids (e.g., linoleic acid, alpha-linolenic acid, dihomo-gamma linolenic acid, and gamma-linolenic acid). It also refers to the presence of merely trace amounts (e.g., less than 1%, less than 0.5%, less than 0.1%, or lower, of the formulation), of such other ingredients that are, or can be, metabolized into omega-3 and/or omega-6 fatty acids. It however allows for the presence of other useful ingredients, e.g., carbohydrates, proteins, vitamins, and/or minerals, which will not significantly effect the omega-3 or omega-6 fatty acid levels of the recipient subject. As such, in one embodiment, the emulsion formulation described herein consists essentially of MCT and the very long chain fatty acids described herein.

The emulsion formulation described herein is used for total daily nutrition treatment, based on a completely enteral and/or parenteral feeding regimen. The recipient is expected to have no other substantial source of nutrients. In one embodiment, the emulsion formulation is a total parenteral formulation. In another embodiment, the emulsion formulation is a total enteral formulation for tube feeding or oral administration. In some embodiments, a combination of enteral and parenteral regimens can be administered to a subject in need. Determination of total daily nutrition for a subject is known to a skilled practitioner. For example, total daily nutrition for a subject can vary with a number of factors, including, but not limited to gender, age, weight, height, lifestyle (e.g., sedentary vs. active), health condition, or a combination thereof.

Total daily caloric content of the emulsion formulation can be determined by the skilled practitioner, for example, from the daily needs of the recipient, e.g., by daily energy expenditure. Typically, calories equal to at least 50% (e.g., 50%, 60%, 70%, 80%, 90%, or higher), up to 100% of the expected energy expenditure of the recipient are contained in the emulsion formulation. In some circumstances, it may be desirable for the formulation to have caloric content that is over 100% of the expected energy expenditure of a recipient subject (e.g., 105%, 110%, 115%, 120%, 130%, 140%, 150%, or higher).

The arachidonic acid content can be determined by the skilled practitioner as well, for example, based on the expected energy expenditure of the recipient. In one embodiment, the arachidonic acid content of the emulsion formulation is from about 0.05% to 2% of expected energy expenditure of a recipient subject. This is sufficient to meet the recipient's essential fatty acid requirement in the absence of, or with inadequate levels of linoleic acid (e.g., less than 1%).

The emulsion formulation can contain additional components required for the total nutrition (e.g., total daily nutrition) of the recipient, such as essential amino acids, as well as essential vitamins and minerals to ensure that the recipient is obtaining all necessary nutrients. Non-limiting examples of such additional components are described herein, and can otherwise be readily determined by the skilled practitioner.

The emulsion formulation can include a protein source or hydrolysate. The protein source or hydrolysate may be any essential or non-essential amino acids, and/or suitable partially hydrolyzed protein or protein hydrolysate utilized in a nutritional formula such as soy protein hydrolysate, casein hydrolysate, whey protein hydrolysate, animal and vegetable protein hydrolysates, partially hydrolyzed whey, casein or soy proteins, and mixtures thereof. Soy or casein protein hydrolysates comprising a substantial proportion of variable chain length peptides, e.g., medium chain and short chain peptides, e.g., di- and tri-peptides, but having less than about 10% free amino acids, possibly less than about 5% free amino acids, are preferred. For greatest use, the protein source can be lactose-free so it can be used for lactose intolerant patients.

When choosing a protein source, it may be optimal to first consider the biological value of the protein, with the highest biological values being found in casein, whey, lactalbumin, egg albumin, and whole egg proteins. Next, the cost can be considered, the lowest cost with the best biological value being the best combination.

The emulsion formulation can include a carbohydrate. The source of carbohydrate may be any simple monosaccharides, disaccharides (e.g. maltose and sucrose), oligosaccharides, polysaccharides, or complex carbohydrates. Examples include fructose, dextrose, glucose, maltodextrin, corn syrup and corn starch. Carbohydrate sources which may be utilized in the formulation described herein include hydrolyzed or nonhydrolyzed starches. Combinations of such carbohydrate sources can also be used. In some embodiments, carbohydrate included in the formulation described herein can include sucrose, cornstarch, dyetrose (a version of dextrose), and any combinations thereof.

The emulsion formulation can include soluble and/or insoluble fibers. Soluble fiber can be metabolized by colonic bacteria to the short-chain fatty acids, acetate, butyrate, and propionate, which serve as an energy source for the colonocytes. Examples of soluble fibers include, but are not limited to, guar gum, and pectin. Examples of insoluble fibers include, but are not limited to soy polysaccharides.

While the dietary formulation for total enteral or parenteral nutrition described herein is intended to be administered as emulsions, other forms of the formulations are also encompassed by the invention. For example, the formulation described herein can be made in powder form by increasing the percent total solids in the formula, using procedures well known to those skilled in the art. The concentrate or powder can be reconstituted for feeding by adding water (tap or deionized-sterilized water) to form an emulsion.

As used herein, the term "emulsion" refers to a mixture of at least two immiscible substances. One of the substances which is referred to as the dispersed phase is dispersed in the other substance referred to as the continuous phase. Emulsions are generally unstable mixtures and do not form spontaneously, thus, in order to mix the continuous and dispersed phases and form the emulsion, an energy input is required. This energy can be applied, for example, by shaking, stirring, homogenizing, spray processing, high pressure pumping and ultrasonic emulsification. The emulsion formulation described herein can be made by blending the fat components listed herein with any proteins, carbohydrates, and/or other additional additives, and homogenizing the mixture into a stable emulsion.

In one embodiment, the emulsion formulation is about 10-50% emulsion, which means that the sole fat components (medium chain triglycerides and very long chain fatty acids) described herein are present in an amount of about 10 g to about 50 g per 100 mL of the formulation. In one embodiment, the emulsion formulation is about 20-40% emulsion, which means that the sole fat components (medium chain triglycerides and very long chain fatty acids) described herein are present in an amount of about 20 g to about 40 g per 100 mL of the formulation. In one embodiment, the emulsion formulation is about 20-30% emulsion, which means that the sole fat components (medium chain triglycerides and very long chain fatty acids) described herein are present in an amount of about 20 g to about 30 g per 100 mL of the formulation. In one embodiment, the emulsion formulation is 20%. In one embodiment, the emulsion formulation is 30%. In one embodiment, the emulsion formulation is 40%.

In one embodiment, the emulsion formulation corresponds to about 10-50% emulsion, and the total calories of the formulation is from about 1000 kcal/kg of the formulation to about 4000 kcal/kg of the formulation. In one embodiment, the emulsion formulation corresponds to about 30-40% emulsion, and the total calories of the formulation is from about 1000 kcal/kg of the formulation to about 4000 kcal/kg of the formulation.

Over time however, the emulsion formed may tend to revert to the stable state of separate oil and aqueous layers. Accordingly, in some embodiments, the emulsion formulation described herein can further comprise any natural or synthetic emulsifier known in the art. The addition of an emulsifier can increase the kinetic stability of emulsions so that, once formed, the emulsion does not change significantly in long term storage.

A variety of suitable emulsifying agents are known in the art. Examples of suitable emulsifying agents include, without limitation, liquid soy lecithin, solid soy lecithin, honey, beeswax, cetyl alcohol, egg phosphatidylcholine, egg lecithin, L-dipalmitoyl phosphatidylcholine (DPPC), DL-dipalmitoyl phosphatidylethanolamine (DPPE), and dioleoyl phosphatidylcholine (DOPC), and combinations thereof. The total concentration of triglycerides as well as free fatty acids in the emulsifier is minimal to non-existent in order to minimize the contribution to the total oil concentration or total fat calories of the emulsion. The total concentration or total calories of triglycerides as well as free fatty acids in the emulsifier can be, for example, less than about 5%, less than about 4%, less than 3%, less than 2%, less than 1%, less than 0.5%, or lower.

Emulsifiers such as soybean phospholipids are commonly used for parenteral products. Emulsifying agents for oil emulsions are generally phospholipids of natural, synthetic or semi-synthetic origin.

Lecithin, such as egg lecithin, can be used as the emulsifying agent. Egg lecithin containing 80-85% phosphatidyl choline and less than about 5% of fat can also be used as an emulsifying agent. One skilled in the art will appreciate that other components may be present in the egg lecithin without adversely affecting the emulsifying properties. For example, the egg lecithin may contain one or more of phosphatidyl ethanolamine, lysophosphatidyl choline, lysophosphatidyl ethanolamine, sphingomeylin and other natural components.

The ratio of lecithin to source oil in the emulsion determines the size of the oil globules formed within the emulsion. In one embodiment, the ratio of lecithin to source oil is from about 1:4 to about 1:20. In one embodiment, the ratio is from about 1:4 to about 1:18. In one embodiment, the ratio is from about 1:4 to about 1:15. In one embodiment, the ratio is from about 1:4 to about 1:10.

The emulsion formulation can contain an emulsifying agent from about 0.5% to about 5% (w/v). The appropriate amount of an emulsifying agent included in the formulation can be determined by the skilled practitioner. In one embodiment, the emulsion contains from about 0.6% to about 2% (w/v) emulsifying agent. In one embodiment, the emulsion contains from about 0.8% to about 1.8% (w/v) emulsifying agent. In one embodiment, the emulsion contains from about 1.0% to about 1.5% (w/v) emulsifying agent. In one embodiment, the emulsion contains from about 1.2% to about 1.4% (w/v) emulsifying agent.

Flavoring may also be added to the emulsion formulation to make it more palatable for enteral use. Flavoring can, for example, be in a form of flavored extracts, volatile oils, chocolate flavoring, peanut butter flavoring, cookie crumbs, vanilla or any commercially available flavoring.

The emulsion formulation may also contain a stabilizer such as carrageenan. Carrageenan increases the viscosity of the formula without forming a gel structure, thus retarding the precipitation of insoluble calcium and phosphorus salts if included in the formula. Xanthan gum or other standard stabilizers may also be used as a stabilizer in the same fashion as carrageenan.

The emulsion formulation can further contain additional components such as, antioxidants, chelating agents, osmolality modifiers, buffers, neutralization agents and the like that improve the stability, uniformity and/or other properties of the formulation.

Suitable antioxidants that can be added include, but are not limited to, alpha-tocopherol (vitamin E) and tocotrienols. As is known in the art, tocotrienols are a natural blend of tocotrienols and vitamin E extract concentrated from rice bran oil distillate, which have an antioxidant activity similar to that of alpha-tocopherol (vitamin E). Tocotrienols have a similar structure to vitamin E and contain three double bonds in the carbon side chain of the molecule.

When used in an emulsion, the concentration of antioxidant added to the emulsion can be, for example, from about 0.002% to about 1.0% (w/v). In one embodiment, the concentration of antioxidant used in the emulsion is from about 0.02% to about 0.5% (w/v).

In one embodiment, tocotrienols can be added as an antioxidant. In another embodiment, about 0.5% (w/v) tocotrienols are added. In one embodiment, vitamin E is added as an antioxidant. In one embodiment, about 0.02% (w/v) vitamin E is added.

The emulsion can also comprise a chelating agent to improve the stability of the emulsion and reduce the formation of oxidized fatty acids. Suitable chelating agents are known in the art and are those that are generally recognized as safe (GRAS) compounds. Examples include, but are not limited to, EDTA. In one embodiment, the emulsion comprises EDTA. In one embodiment, the emulsion comprises concentrations of EDTA between about $1 \times 10^{-6}$ M and $5 \times 10^{-5}$ M.

An osmolality modifier can also be incorporated into the emulsion formulation to adjust the osmolality to a value suitable for parenteral administration. Amounts and types of osmolality modifiers for use in parenteral formulations are well-known in the art. An example of a suitable osmolality modifier is glycerol. The concentration of osmolality modifier typically ranges from about 2% to about 5% (w/v). In one embodiment, the amount of osmolality modifier added is between about 2% and about 4%. In one embodiment, the amount of osmolality modifier added to the formulation is between about 2% and about 3%. In one embodiment, about 2.25% (w/v) glycerol is added as an osmolality modifier. The final product should preferably be isotonic so as to allow infusion of the formulation through either a central or peripheral venous catheter.

One skilled in the art will understand that the pH of the formulation can be adjusted through the use of buffers or neutralization agents. Emulsions with pH values close to physiological pH or above have been shown to be less prone to fatty acid peroxidation. One skilled in the art will appreciate that the pH of the formulation can be adjusted through the use of an appropriate base that neutralizes the negative charge on the fatty acids, through the use of an appropriate buffer, or a combination thereof. A variety of bases and buffers are suitable for use with the emulsion formulation described herein. One skilled in the art will appreciate that the addition of buffer to the emulsion will affect not only the final pH, but also the ionic strength. High ionic strengths may negatively impact the zeta potential of the emulsion (i.e., the surface charge of the oil globules) and are, therefore, less desirable.

Selection of appropriate buffer strength to provide a suitable pH and zeta potential is considered to be within the ordinary skills of a worker in the art. In one embodiment, the pH of the formulation is adjusted using sodium hydroxide. In one embodiment, the pH is adjusted with a buffer. In one embodiment, the buffer is a phosphate buffer. In another embodiment, both sodium hydroxide and a phosphate buffer are added to the formulation. The final pH of the formulation is typically between about 6.0 and about 9.0. In one embodiment, the pH of the formulation is between about 7.0 and about 8.5. In one embodiment, the pH of formulation is between about 7.0 and about 8.0.

The emulsion formulation can also include a therapeutic agent beyond the various components already discussed. A "therapeutic agent" as the term is used herein refers to a physiologically or pharmacologically active substance that produces a localized or systemic therapeutic effect or effects in a subject and refers generally to drugs, nutritional supplements, vitamins, minerals, enzymes, hormones, proteins, polypeptides, antigens and other therapeutically useful compounds beyond the various components already discussed herein.

The emulsion formulation may comprise a diagnostic agent.

The emulsion formulation described herein can be prepared by any number of conventional techniques known to those skilled in the art. In general, the core lipid is first mixed with the emulsifier and the antioxidant, if one is being used. The emulsion is then prepared by slowly adding an oil phase into an aqueous phase with constant agitation. If an osmolality modifier is being used, it is added to the water prior to mixture with the oil phase. The pH can be adjusted at this stage, if necessary, and the final volume adjusted with water, if required.

Container design is also an important factor when manufacturing the emulsion formulation described herein. If the emulsion is packaged in glass, it is preferably done in a container that is filled with nitrogen before the actual emulsion is added. After addition of the emulsion, the glass container can be filled again with nitrogen to remove dead space when the cap is affixed. Such nitrogen filling prevents peroxide formation. If the product is packaged in plastic, a DEHP-free container that is gas impermeable is preferred. In one embodiment, the container also has the appropriate overwrap to minimize peroxide formation in the lipids as well as leaching of the plasticizer from the container into the product itself. In addition, if plastic is used, it is desirable to have a desiccant in with the bag as well as an indicator that notes if there is an air leak in the overwrap. In some embodiments, the container is also latex-free.

Uses of the emulsion formulation to provide total nutrition to a subject

The emulsion formulation described herein can provide sufficient essential fatty acids to meet the needs for maintenance and/or growth of a subject, while minimizing the subject's risk of developing systemic inflammatory response (e.g., from endotoxin). As such, administration of the emulsion formulation described herein can be used for overall nutrition, and/or for reducing or minimizing a subject's propensity for developing a systemic inflammatory response. One aspect of the invention relates to a method for providing total enteral or parenteral nutrition to a subject that minimizes the human subject's propensity for developing a systemic inflammatory response. The method involves administration of the emulsion formulation described herein to a subject so that they receive the daily allotment of components every 24 hours. The total emulsion formulation can be given to the subject all at once (e.g., in a single dose), infused slowly over a longer period of time, or broken into separate doses (e.g., ⅓, ⅓, ⅓) and given all doses over a 24-hour period. Determination of the appropriate administration regimen can be determined by the skilled practitioner.

Administration can be performed for a period of time determined necessary by the skilled practitioner. In one embodiment, administration is over a period of time required to produce a desired reduction in inflammation or a decreased propensity for developing an inflammatory response (e.g., systemic). The duration of administration can be long term, e.g., for the rest of the life of the subject, or it can be administered episodically. In some cases (e.g. acute conditions) it may be possible to discontinue administration of the emulsion formulation described herein at some point without recurrence or worsening of symptoms. Prolonged administration may be necessary in other circumstances (e.g., chronic conditions) to produce a continued therapeutic effect. Appropriate dosages and administration regimens can readily be determined by one skilled in the clinical arts. In some embodiments, the administration can be performed for at least about 1 week or longer, including, e.g., at least about 2 weeks, at least about 3 weeks, at least about 1 month, at least about 2 months, at least about 3 months, at least about 4 months, at least about 5 months, at least about 6 months or longer.

The various formulation embodiments described herein can be used to produce a reduction in inflammation or decreased propensity for developing a systemic inflammatory response in a recipient subject. The optimal formulation for use can be determined on a case by case basis for each individual, taking into consideration factors and circumstances specific to the individual (e.g. the specific desired results, previous diet, the specific physical condition of the individual). A reduction in inflammation or a decreased propensity for developing a systemic inflammatory response resulting from the administration can be determined by the skilled practitioner. Guidance and examples of measuring inflammation, is provided herein.

Inflammation which is to be reduced may be ongoing (e.g. from a pre-existing condition or disease) or expected to be likely to develop (e.g., from exposure to a substance, increase risk of disease development, or expected procedures such as surgical procedures). Ongoing inflammation may be the result of, or the cause of, a disease or disorder, or may merely be associated with a disease or disorder of the individual. As such, some aspects described herein relate to a variety of methods of treatment and/or prevention of a variety of conditions in an individual. Without limitation, such conditions include essential fatty acid deficiency, parenteral nutrition associated liver disease, hypertriglyceridemia, traumatic brain injury, inflammatory diseases or disorders, fatty liver disease, obesity, intestinal failure, diabetes, metabolic syndrome, or any combinations thereof. In some embodiments, the emulsion formulation described herein is used to minimize the risk of infection (e.g., sepsis), to reduce the fat content of a liver in a liver donor, and/or to treat essential fatty acid deficiency.

While the methods described herein can benefit a wide range of individuals, some subjects will be particularly in need of administration of the emulsion formulation described herein. In one embodiment, the method described herein includes identification of a subject in need of a total nutrition (e.g., a total enteral or parenteral nutrition) that minimizes the subject's propensity for developing a systemic inflammatory response, followed then by administration of the emulsion formulation every 24 hours at all once or in separate doses. A subject in need can be a subject who has essential fatty acid deficiency, an intestinal failure, parenteral nutrition associated liver disease, fatty liver disease, hypertriglyceridemia, traumatic brain injury, inflammatory disease or disorder, or combinations thereof. A subject in need can also be a pregnant woman or a subject who is likely to develop an inflammatory disease or disorder or who will undergo or has undergone hemodialysis, surgery/operation, or invasive procedures such as catheterization or intubation. In some embodiments, a subject in need is a subject who has detectable adverse inflammation (e.g. detectable by one or more means known in the art, some of which are described herein), or a subject who has a disease or pathology or condition associated with adverse inflammation. In some embodiments, a subject in need can also be a subject with an increased likelihood (e.g., from a genetic predisposition, behavioral, or environmental effects) for development of a condition resulting from, producing, or associated with adverse inflammation. A subject in need, may further be a subject in need of a liver transplant, or a subject who plans to donate a liver, or have another operation, or is otherwise at increased risk for infection (e.g., is immunocompromised). Such a subject can be determined by the skilled practitioner through known means of diagnosis.

In one embodiment, the subject in need is a pediatric subject with intestinal failure. In this embodiment, the emulsion formulation can simultaneously prevent essential fatty acid deficiency, reduce the risk of parenteral nutrition associated liver disease, and decrease systemic inflammatory response in such vulnerable population.

In one embodiment, the subject in need is critically ill. The subject can be critically ill for a variety of reasons including surgery, burns, trauma, cancer (e.g., pancreatic cancer, colon cancer, stomach cancer, esophageal cancer, lung cancer, ovarian cancer, brain cancer, leukemia and lymphoma), AIDS, multisystem organ failure, sepsis or inflammatory process which can impair fatty acid elongation and desaturation. It is also useful for individuals who may have an infection at the time of the administration of the emulsion formulation or may be at high risk of infection due to some sort of immunocompromise. Individuals at risk of infection include those suffering with secondary immunosuppression due to chemotherapy or diabetes mellitus, protein-malnourished patients, or patients undergoing surgery, e.g., abdominal or thoracic surgery.

In some aspects, administration of the formulation described herein to a subject in need thereof, is a form of treatment of that subject for the condition that causes the need. As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. For methods of prevention, a subject to be administered the emulsion formulation is generally a subject at risk for a systemic inflammatory response or an inflammatory condition due to genetic predisposition, diet, exposure to disorder-causing agents, exposure to pathogenic agents, operation/surgery, and the like. The term "treat" or "treatment" refer to therapeutic treatment, wherein the object is to slow down the development or spread of disease or symptoms. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also refer to prolonging survival as compared to expected survival if not receiving treatment.

The term "subject", "individual", and "patient" are used interchangeably herein, and refer to an animal, especially a mammal, for example a human, to whom treatment, with a composition as described herein, is provided. The term "mammal" is intended to encompass a singular "mammal" and plural "mammals," and includes, but is not limited: to humans, primates such as apes, monkeys, orangutans, and chimpanzees; canids such as dogs and wolves; felids such as cats, lions, and tigers; equids such as horses, donkeys, and zebras, food animals such as cows, pigs, and sheep; ungulates such as deer and giraffes; rodents such as mice, rats, hamsters and guinea pigs; and bears. In some embodiments, the subject is a human subject, including adults, infants, children, and elderly. Accordingly, the emulsion formulation and methods described herein can be used in adults, infants, children and/or elderly.

As used herein, the term "systemic inflammatory response" refers to an inflammatory state affecting the whole body of a subject. In one embodiment, a systemic inflammatory response is a response of a subject's immune system to infection. In other embodiments, a systemic inflammatory response is a response of a subject's immune system to a non-infectious disease or disorder (e.g., but not limited to, essential fatty acid deficiency, parenteral nutrition associated liver disease, fatty liver disease, hypertriglyceridemia, intestinal failure, traumatic brain injury, or any combinations thereof). Systemic inflammatory responses include, but are not limited to, (a) a body temperature greater than 38° C. or less than 36° C.; (b) a heart rate greater than 90 beats per minute; (c) tachypnea, as manifested by a respiratory rate of greater than 20 breaths per minute or hyperventilation, as indicated by a Paco2 less than 32 torr (less than 4.3 kPa); (d) an alteration of the white blood cell count of greater than 12,000 cells/mm$^3$, less than 4,000 cells/mm$^3$, or the presence of greater than 10% immature neutrophils (band forms), and any combinations thereof.

The term "inflammatory disease or disorder" as used herein, refers to any disorder that is either caused by inflammation or whose symptoms include inflammation, or is otherwise associated with inflammation. One such inflammatory disorder caused by inflammation is septic shock, and an inflammatory disease whose symptoms include inflammation is rheumatoid arthritis. Inflammation is associated with a number of diseases or disorders, for example, neurodegenerative diseases, cardiovascular disease or disorders, and infectious diseases. The inflammatory disorders of the present invention include but are not limited to: diabetes-associated nephropathy and retinopathy, protein wasting, muscle fatigue or inflammation, coronary artery disease, inflammatory bowel disease, atherosclerosis and other cardiovascular diseases, Alzheimer's disease, myocarditis, cardiomyopathy, pancreatitis, HIV disease and AIDS, complication of AIDS or cancer therapy, celiac disease, cystic fibrosis, acute endocarditis, pericarditis, hepatitis, Systemic Inflammatory Response Syndrome (SIRS)/sepsis, adult respiratory distress syndrome (ARDS), asthma, rheumatoid arthritis, osteoarthritis, systemic lupus erythematosis, airway hyperresponsiveness (AHR), bronchial hyperreactivity, chronic obstructive pulmonary disease (COPD), congestive heart failure (CHF), inflammatory complications of diabetes mellitus, inflammatory bowel disease (CROHN's disease and/or ulcerative colitis) to either induce remission and/or prevent relapse, metabolic syndrome, non-alcoholic fatty liver disease, end stage renal disease (ESRD), and dermatitis. Another inflammatory condition which can be treated is major burns (e.g. second or third degree burns). In one embodiment, the major burns cover more than 20% body surface area. Another inflammatory condition which can be treated is traumatic brain injury (e.g. with a Glasgow Coma Score less than 8). Multiple trauma as well as any critical illness producing APACHE III scores of greater than 10 can also be treated. Another condition which can be treated by the methods of the present invention is receipt of a stem cell transplant or a bone marrow transplant.

"Inflammation" or "inflammatory symptoms" refers to one or more biological and physiological sequelae including: vasodilatation; increased vascular permeability; extravasation of plasma leading to interstitial edema; chemotaxis of neutrophils, macrophages and lymphocytes; cytokine production; acute phase reactants; C-reactive protein (CRP); increased erythrocyte sedimentation rate; leukocytosis; fever; increased metabolic rate; impaired albumin production and hypoalbuminemia; activation of complement; and stimulation of antibodies.

As used herein, "cardiovascular disease" includes diseases associated with the cardiopulmonary and circulatory systems including but not limited to ischemia, angina, edematous conditions, artherosclerosis, CHF, LDL oxidation, adhesion of monocytes to endothelial cells, foam-cell formation, fatty-streak development, platelet adherence, and aggregation, smooth muscle cell proliferation, reperfusion injury, high blood pressure, and thrombotic disease.

As used herein, a "symptom" of an inflammatory condition includes physical symptoms (pain, edema, erythema, and the like) associated with a particular inflammatory condition, and/or biomarkers associated either generally with inflammation or particularly with a specific inflammatory condition.

Another aspect of the invention relates to a method of reducing the level of one or more inflammatory biomarkers in a subject that correlates to an inflammatory condition. The method comprises administering to the subject the emulsion formulation described herein, wherein the formulation is administered in an amount sufficient to reduce the level of the inflammatory biomarker(s). The method may involve identification and/or determination of the level of the biomarker(s) prior to initial administration, and also may involve such determination throughout the course of the administration, for example, to determine/verify the reduction occurs.

"Inflammatory biomarkers that correlate with an inflammatory condition," and also "inflammatory biomarkers" include, but are not limited to CRP, cytokines associated with inflammation, such as members of the interleukin family, including IL-1 through IL-17 that are associated with inflammation, TNF-alpha; B61; certain cellular adhesion molecules, such as for example, e-selectin (also known as ELAM), sICAM, integrins, ICAM-1, ICAM-3, BL-CAM, LFA-2, VCAM-1, NCAM and PECAM; neopterin; serum procalcitonin; leukotriene, thromboxane, and isoprostane.

In particular, elevated levels of CRP are associated with cardiovascular diseases and disorders, infectious diseases, such as, myocarditis, cardiomyopathy, acute endocarditis, or pericarditis; SIRS; diabetes; metabolic syndrome; muscle fatigue, injury or inflammation; and systemic inflammation.

Other inflammatory biomarkers that correlate with inflammatory disease include: Elevated levels of IL-6, sTNFr2 and CRP are associated with type II diabetes, muscle inflammation and ESRD; elevated levels of cellular adhesion molecules are associated with systemic inflammation; elevated levels of IL-1 and TNF-alpha are associated with IDDM and NDDM associated inflammation; elevated levels of IL-10 and IL-6 are associated with SIRS; elevated levels of neopterin are associated with SIRS; elevated levels of procalcitonin are associated with systemic inflammation.

Other proteins or markers associated with inflammation include serum amyloid A protein, fibrinonectin, fibrinogen, leptin, prostaglandin E2, serum procalcitonin, soluble TNF receptor 2, elevated erythrocyte sedimentation rate, and elevated white blood count, including percent and total granulocytes (polymorphonuclear leukocytes) monocytes, lymphocytes and eosinophils.

In one embodiment, the inflammatory biomarker is selected from the group consisting of C-reactive protein (CRP), interleukin-1-alpha (IL-1-alpha), interleukin-1-beta (IL-1-beta), interleukin-6 (IL-6), soluble TNF receptors I and II, oxidative metabolites of protein, carbohydrate, fat, DNA, and elevated white blood cell count (WBC).

The emulsion formulation is to be administered over an effective regimen. As the term is used herein, the term "regimen" is used to refer to the systematic plan of administration of the dietary formulation. As such, the regimen includes the dose per specific administration, the time course of each administration, the time period between individual administrations, the time period over which a specific dose is used, and coordination of other therapies or medications or procedures. Dosage may beneficially be adjusted over time. For example, initial dosage may contain extremely low to no arachidonic acid, to rapidly reduce extremely high levels in an individual. Following the desired reduction, the amounts of arachidonic acid may be increased to levels that will maintain the desired levels in the individual. The individual can be monitored over the course of the regimen to track fatty acid levels, and the dosage can be adjusted accordingly.

The term "effective regimen" as used herein means that an "effective amount" is administered over an effective course (a sufficient dose or amount over a sufficient period of time) to achieve a final concentration in the body sufficient to produce the desired results (e.g., of reducing inflammation or minimizing risk of a systemic inflammatory response). Such an "effective regimen" leads to a statistically significant reduction in one or more symptoms of inflammation or systemic inflammation response. An effective regimen may result in a reduction of one or more markers of disease, and/or may result in complete prophylaxis or elimination of one or more symptoms. More specifically there may be at least about 30%, at least about 50%, at least about 70%, at least about 80%, and at least about 90% reduction in the markers or symptoms as measured by convention means (e.g., in the levels of inflammatory biomarkers associated with inflammation, systemic inflammatory response, or an inflammatory condition, and/or a reduction in one or more symptoms associated with inflammation such as pain and/or edema associated with inflammation).

By "amount sufficient to reduce the level of inflammatory biomarker" is meant that the formulation is administered in an "effective regimen", which is to say an "effective amount" is administered over an effective course (a sufficient dose or amount over a sufficient period of time) to achieve a final concentration in the body sufficient for reducing inflammation or systemic inflammatory response as measured by a reduction in the amount of an inflammatory biomarker.

An "effective amount" is an amount sufficient to produce beneficial or desired results in a subject. An effective amount can be administered in one or more administrations. For purposes of this invention, an effective regimen is a course of administration of an effective amount of the formulation sufficient to ameliorate, stabilize, reverse, slow or delay the progression or onset of the disease or disorder, e.g. fatty liver disease, essential fatty acid deficiency, obesity, diabetes, cardiovascular disease, or inflammatory disorder. The beneficial or desired results can be measured by monitoring the reduction in or disappearance of one or more symptoms of the disease or disorder. One of skill in the art will recognize that an effective amount does not require complete recovery or complete prevention of a symptom, but merely a significant, sustainable, measurable reduction. Preferably one or more symptoms are reduced by at least about 30%. In one embodiment, one or more symptoms are reduced by at least about 50%. In one embodiment, one or more symptoms are reduced by at least about 70%, at least about 80%, or at least about 90% measurable reduction in a symptom.

Amelioration of symptoms due to inflammation or systemic inflammatory response can be quantified by one or more assays known in the art. For example, a statistically significant reduction in CRP levels and/or reduction in cytokines such as, but not limited to interleukins 1-17 (IL 1-17) associated with inflammation; and TNF-alpha. A clinical analysis which tracks a combination of two or more such markers of inflammation may also prove useful in analysis of symptom reduction. Such assays are well known to those skilled in the art (see for example, U.S. Pat. Nos. 5,688,656; 6,040,147; 6,180,643; 5,993,811; 6,103,702; 6,203,997, 5,496,832; 5,780,237 and U.S. Patent application publications 2005/0137253 and 20010007022, which are herein incorporated by reference in their entirety).

C-reactive protein (CRP) serves as an exemplary marker for systemic inflammation. See U.S. Pat. No. 6,040,147. In humans CRP levels are elevated during inflammatory disorders such as infection, trauma, surgery, tissue infarction, and in IDDM patients without macrovascular disease. The magnitude of the increase varies from about 50% to as much as 100-fold during systemic inflammation (Gabay, C., et al., New Engl. J. Med. 340: 448-454, 1999). Recent evidence has shown that CRP is also a risk factor for cardiovascular disease and stroke where inflammation plays an important role (Lagrand, W. K., et al, Circulation 100: 96-102, 1999). Most CRP production is from hepatocytes in response to pro-inflammatory cytokines, especially interleukin-6 and 1.quadrature. (Ganter, U., et al., EMBO J. 8: 3773-3779, 1989), although macrophages have also been reported to release CRP (Dong, Q, et al, J. Immunol. 156: 481504820, 1996).

Surrogate markers of inflammation in diabetic patients include glycosylated hemoglobin (HbAlc) and advanced glycation endproducts (AGEs) that are formed from glycosylated hemoglobin and related compounds. Additional biomarkers of inflammation in diabetes include arachidonate (5, 8, 11, 14 eicosatetraenoic acid, an essential omega-6 highly unsaturated fatty acid that provides both critical structural properties to membranes, and which, when released from phospholipids, functions as the primary substrate for eicosanoid (prostaglandin, thromboxane, leukotriene) synthesis. Arachidonate has been linked to many processes that are implicated in type-2 diabetes, such as insulin release from the pancreas, insulin action in skeletal muscle and insulin sensitivity.

In one embodiment, the disease to be prevented or treated is fatty-liver disease. As such, another aspect of the invention relates to a method for preventing or treating fatty-liver disease in a subject. The method comprises administering an effective regimen of the emulsion formulation described herein. The method may further comprise determination of a subject in need of such treatment or prevention, followed by beginning the course of administration. As used herein "fatty-liver disease" refers to a disease wherein fat (hepatocytes) is excessively accumulated in the liver and can cause severe diseases such as chronic hepatitis and hepatic cirrhosis. In patients with fatty liver disease, lipids, particularly neutral fat, accumulate in hepatocytes to the extent that the amount exceeds the physiologically permissible range. From a biochemical point of view, a standard for judgment of fatty liver is that the weight of neutral fat is about 10% (100 mg/g wet weight) or more of the wet weight of hepatic tissue. A significant reduction in the liver fat content of a fatty liver is another indicator of amelioration of symptoms. Any reduction in fat content is beneficial. Preferably the reduction is at least 5%, at least 10%, at least 20%, at least 30%, at least 40%, at least 50%, at least 60%, at least 70%, at least 80%, or at least 90%.

Fatty liver disease is generally detected by observation of elevated serum levels of liver-specific enzymes such as the transaminases ALT and AST, which serve as indices of hepatocyte injury, as well as by presentation of symptoms, which include fatigue and pain in the region of the liver, though definitive diagnosis often requires a biopsy. Fatty-liver disease is also associated with parenteral nutrition; this disease includes both biochemical, i.e., elevated serum aminotransferases, bilirubin, and alkaline phosphatase, and histologic alterations such as steatosis, steatohepatitis, lipidosis, cholestasis, fibrosis, and cirrhosis.

Detectable, sustained reduction in serum levels of such transaminases ALT and AST, and/or of aminotransferases, bilirubin, and alkaline phosphatase would serve as another indicator of amelioration of symptoms by administration of the formulation described herein. A "sustained reduction" as the term is used herein refers to a statistically significant, repeatedly observable detected reduction, over an established period of time (e.g. days, weeks, months).

In vivo animal models of varied diseases and disorders are known in the art and may be used to determine the efficacy of the formulation, or treatment protocols. For example, U.S. Pat. No. 6,103,702 describes a model for systemic inflammatory response syndrome (SIRS) and sepsis, where the efficacy of treatment in vivo may be determined through monitoring the level of TNF-α in tissues such as spleen and liver or in serum; U.S. Pat. Nos. 6,193,957; 6,051,566; 5,080,899, 6,180,643, 6,028,208 and U.S. Pat. App. Nos. 20010000341, 20010006656 describe models and protocols for determining the efficacy of treatments for conditions associated with pulmonary or respiratory inflammation; U.S. Pat. No. 5,789,652 is directed to a non-insulin dependent diabetic rat which can be used to determine the efficacy of test compounds in the treatment of the diabetes; models for fatty liver and excessive weight gain with insulin resistance are also known.

Enteral feeding literally means using the gastrointestinal tract for the delivery of nutrients, which includes eating food, consuming oral supplements and all types of tube feeding. Methods of administering emulsions to patients for total enteral nutrition are known in the art. The routes most often used are naso-gastric tubes (NGT) and percutaneous endoscopic gastrostomy (PEG) tubes. Other routes that are increasingly being used include naso-jejunal and jejunostomy feeding, which may be the only feasible route if it is not appropriate to feed via the stomach. A skilled artisan understands dosages necessary for total enteral nutrition (e.g., daily nutrition). The dosage is to provide sufficient energy to provide energy balance or caloric needs of a recipient patient. For example, the calorie needs for an adult patient generally ranges from 15-40 kilocalories/kg weight of the patient. For an infant patient, the caloric needs may be up to 150 kilocalories/kg weight of the patient (e.g., from about 80 kilocalories/kg to about 150 kilocalories/kg weight of the patient). The duration of the administration can be either short term (e.g. days to several weeks or months) or long-term (e.g. years to permanent).

Total parenteral nutrition (TPN), is the practice of feeding a person intravenously, circumventing the gut. Methods of administering oil emulsions to patients for total parenteral nutrition (PN) applications or therapeutic benefit are known in the art. Typically the emulsions are administered by infusion over a suitable period of time. The preferred method of delivering TPN is with a medical infusion pump. A sterile bag of nutrient solution, between 500 mL and 4 L is provided. The pump infuses a small amount (0.1 to 10 mL/hr for pediatric applications or at rates of 40 cc/hour up to 120 cc/hour, depending on fluid requirements, for adults) continuously in order to keep the vein open. Feeding schedules vary, but one common regimen ramps up the nutrition over a few hours, levels off the rate for a few hours, and then ramps it down over a few more hours, in order to simulate a normal set of meal times.

For treatment of diseases and disorders, e.g., essential fatty acid deficiency and inflammatory diseases or disorders, obesity, etc., or for methods for increasing immunity or minimizing the risk of infection, any form of administration known in the art may be used. When total enteral or parenteral nutrition is used, the emulsion formulation described herein preferably also contains all essential amino acids, as well as essential vitamins and minerals to insure that the patient is obtaining necessary nutrients.

Another aspect of the invention relates to a method for treating a subject prior to, and/or following, a surgical procedure. Such methods are analogous to the other methods of treatment described herein. In treating a liver transplant donor, the emulsion formulation can be administered prior to the donation of the liver. Preferably, administration is for a period of time sufficient to reduce the fat content of a liver, e.g., the formulation may be given orally or enterally for four to six weeks, or intravenously for four to five days prior to liver donation. Other administration protocols can be used and can readily be determined by one skilled in the clinical arts. Subjects may also be treated prior to a surgical procedure, e.g., the formulation may be given orally or enterally for four to six weeks, or intravenously for four to seven days prior to surgery. Other administration protocols can be used and can readily be determined by one skilled in the clinical arts. Administration to the donor may also be performed after liver transplant during postoperative recovery. This can occur even when the donor did not receive administration prior to donation.

A liver transplant recipient can be likewise administered the formulation described herein, pre-operatively, and/or post-operatively.

Another aspect of the invention relates to kits containing the emulsion formulation. The kit would provide an appropriate dosing regimen for a prescribed period. The kit can comprise one or more packages or containers containing the dietary formulation in combination with a set of instructions, generally written instructions, relating to the use and dosage of the formulation. The packages containing the formulation may be in the form of unit doses or pharmacy bulk packages. The doses may be packaged in a format such that each dose is associated, for example, with a particular time period prescribed for administration. There may also be associated with the kit a notice in the form prescribed by a governmental agency regulating the manufacture, use or sale of biological products, which notice reflects approval by the agency of manufacture, use or sale for human or animal administration.

Embodiments of various aspects described herein can be defined in any of the following numbered paragraphs:

1. An emulsion formulation for total enteral or parenteral nutrition of a human subject comprising as the sole fat components:
   (i) medium chain triglycerides; and
   (ii) very long chain fatty acids selected from the group consisting of (a) very long chain omega-3 polyunsaturated fatty acids (VLC omega-3 PUFAs) and (b) docosahexaenoic acid (DHA) and arachidonic acid (AA) in a ratio of about 10:1 (v/v or w/w) to about 2000:1 (v/v or w/w);
   wherein the sole fat components provide about 10% to about 90% total calories of the formulation, and
   wherein the medium chain triglycerides provide about 25%-95% total fat calories.
2. The emulsion formulation of paragraph 1, wherein the sole fat components are present in an amount of about 10 g to about 50 g per 100 mL of the formulation.
3. The emulsion formulation of paragraph 2, wherein the sole fat components are present in an amount of about 20 g to about 30 g per 100 mL of the formulation.
4. The emulsion formulation of paragraph 2 or 3, wherein the total calories of the formulation is from about 1000 kcal/kg of the formulation to about 4000 kcal/kg of the formulation.
5. The emulsion formulation of any one of paragraphs 1-4, wherein the medium chain triglycerides and the very long chain fatty acids are present in a weight ratio of at least about 1:1 or higher.
6. The emulsion formulation of paragraph 5, wherein the weight ratio of the medium chain triglycerides and the very long chain fatty acids is about 50:50.
7. The emulsion formulation of paragraph 5, wherein the weight ratio of the medium chain triglycerides to the very long chain fatty acids is about 70:30.
8. The emulsion formulation of any one of paragraphs 1-7, wherein the medium chain triglycerides have a carbon length of 6, 8, and/or 10.
9. The emulsion formulation of any one of paragraphs 1-8, wherein the very long chain fatty acids provide about 2-10% total calories of the formulation.
10. The emulsion formulation of any one of paragraphs 1-9, wherein the very long chain fatty acids provide about 3% total calories of the formulation.

11. The emulsion formulation of any one of paragraphs 1-10, wherein the VLC omega-3 PUFAs are selected from the group consisting of docosahexaenoic acid (DHA), eicosapentaenoic acid (EPA), eicosatrienoic (stearidonic) acid, and 5-docosapentaenoic acid (DPA), and combinations thereof.
12. The emulsion formulation of any one of paragraphs 1-11, wherein the very long chain fatty acids are VLC omega-3 PUFAs.
13. The emulsion formulation of any one of paragraphs 1-12, wherein the very long chain fatty acids are docosahexaenoic acid (DHA) and arachidonic acid (AA) in a ratio of about 20:1 (v/v or w/w).
14. A method of providing total enteral or parenteral nutrition to a human subject in need thereof that minimizes the human subject's propensity for developing a systemic inflammatory response, consisting essentially of administration of an emulsion formulation of any one of paragraphs 1-13 every 24 hours.
15. The method of paragraph 14, wherein the administration is performed for at least 1 week.
16. The method of paragraph 14 or 15, wherein the administration is performed for at least 1 month.
17. The method of any one of paragraphs 14-16, wherein the human subject in need thereof has essential fatty acid deficiency.
18. The method of any one of paragraphs 14-17, wherein the human subject in need thereof has an intestinal failure.
19. The method of any one of paragraphs 14-18, wherein the human subject in need thereof has a parenteral nutrition associated liver disease.
20. The method of any one of paragraphs 14-19, wherein the human subject in need thereof has a fatty liver disease.
21. The method of any one of paragraphs 14-20, wherein the human subject in need thereof has hypertriglyceridemia.
22. The method of any one of paragraphs 14-21, wherein the human subject in need thereof has traumatic brain injury.
23. The method of any one of paragraphs 14-22, wherein the human subject in need thereof is a pregnant woman.
24. The method of any one of paragraphs 14-23, wherein the human subject in need thereof has or is likely to develop an inflammatory disease or disorder.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%. When "0%" is used to describe the amount of a component, it is understood that this includes situations where only trace amounts of the component are present.

All patents, patent applications, and publications identified in this document are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples are not intended to limit the scope of the invention, but are rather intended to be exemplary of certain embodiments.

Example 1

The Addition of Medium-Chain Triglycerides to a Purified Fish Oil-Based Diet Alters Inflammatory Profiles in Mice Parenteral nutrition associated liver disease (PNALD) is a deadly complication of long term parenteral nutrition (PN) use in infants. Fish oil-based lipid emulsion has been shown in recent years to effectively treat PNALD. In this Example, a murine model was used to study several dietary lipids including soybean oil, purified fish oil (PFO), coconut oil (HCO) and medium-chain triglycerides (MCT) to determine the effects of these lipid sources on growth, serum essential fatty acid levels, liver histology, and inflammatory profiles with and without an endotoxin challenge. Importantly, purified fish oil differs from fish oil in that it has had the fatty acids with carbon lengths lower than C20 removed. This allows for the analysis of the effects of a diet having only very long chain fatty acids as the fatty acid component.

Exemplary Methods and Materials

Animals and diets. Adult male C57/B16 mice (Jackson Laboratories, Bar Harbor Me.) were housed five to a cage and maintained in a climate-controlled facility with a 12:12-hour light-dark cycle for a period of four days of acclimation prior to experimentation. During this period, animals had free access to water and a standard rodent chow diet. Experimental protocols were approved by the Boston Children's Hospital Institutional Animal Care and Use Committee. Animals were then assigned by cage to one of the following six dietary treatment groups (10 animals per group) based on fat content by weight: 10.84% soybean oil (SOY), 10% coconut oil (HCO), 10% medium-chain triglycerides (MCT), 3% purified fish oil (PFO), 3% purified fish oil with 3% medium-chain triglycerides (50:50 MCT:

PFO) and 3% purified fish oil with 7.59% medium-chain triglycerides (70:30 MCT:PFO).

Purified fish oil was derived primarily from sardine oil from which all saturated fat and fats with carbon lengths less than 18 were removed, and was obtained from Pronova BioPharma/BASF (Lysaker, Norway). Medium-chain triglyceride (MCT) oil was purchased from Health and Sport, LLC (Amston, Conn.). All diets were provided in pelleted form. Equivalent amounts of casein, L-cystine, sucrose, dyetrose (a version of dextrose which allows the diet to be easily pelleted), and vitamin and mineral mixtures were included in all diets. There were slight variations in corn starch and cellulose among the diets to make the diets as nearly isocaloric as possible. Total kcal/kg was slightly lower in the PFO and 50:50 MCT:PFO diets. Table 1 below lists the six different dietary composition (in grams per kg of the composition).

TABLE 1

Dietary compositions (grams per kg)

| | MCT | HCO | SOY | PFO | 50:50 MCT:PFO | 70:30 MCT:PFO |
|---|---|---|---|---|---|---|
| Casein | 140 | 140 | 140 | 140 | 140 | 140 |
| L-Cystine | 1.8 | 1.8 | 1.8 | 1.8 | 1.8 | 1.8 |
| Sucrose | 100 | 100 | 100 | 100 | 100 | 100 |
| Cornstarch | 405.68 | 405.68 | 405.68 | 481.58 | 451.58 | 405.68 |
| Dyetrose | 155 | 155 | 155 | 155 | 155 | 155 |
| Medium Chain Triglycerides | 108.4 | 0 | 0 | 0 | 30 | 75.9 |
| Purified Fish Oil | 0 | 0 | 0 | 30 | 30 | 30 |
| Soybean Oil | 0 | 0 | 100 | 0 | 0 | 0 |
| Hydrogenated Coconut Oil | 0 | 100 | 0 | 0 | 0 | 0 |
| t-Butylhydroquinone | 0.02 | 0.02 | 0.02 | 0.02 | 0.02 | 0.02 |
| Cellulose | 41.6 | 50 | 50 | 44.1 | 44.1 | 44.1 |
| Mineral Mix #210050 | 35 | 35 | 35 | 35 | 35 | 35 |
| Vitamin Mix #310025 | 10 | 10 | 10 | 10 | 10 | 10 |
| Choline Bitartrate | 2.5 | 2.5 | 2.5 | 2.5 | 2.5 | 2.5 |
| Total kcal per kg | 3925.7 | 3925.9 | 3925.9 | 3569.2 | 3710.2 | 3925.9 |

Experimental design. Animals were pair-fed the experimental diets in groups of 5 for a period of 12 weeks. Individual body weight and total cage food intake were recorded every three days for the duration of the study period. Food intake was controlled by the lowest food intake among the six groups at each time to ensure that there were no differences in food intake across the six dietary groups. Blood samples were obtained from each animal prior to initiation of dietary treatment and again at 2, 4, 6, 9, and 12 weeks after diet initiation. At the end of 12 weeks, animals in each dietary group were divided into two subgroups: one group received an intraperitoneal (IP) injection of lipopolysaccharide (LPS) 150 μg in saline (1 μg/μL) and the second group received an IP saline injection of equivalent volume. Four hours after receiving lipopolysaccharides (LPS) or saline, blood samples were obtained via retro-orbital venous access and animals were euthanized. Livers were immediately harvested and lobes were divided into three sections: one was prepared for H&E staining as described by Lillie (25), a second for oil red O staining as described by Bancroft (26), and a third was snap frozen and stored at −80 C for later analysis. Liver slides were reviewed by a single blinded board-certified pathologist for qualitative analysis.

Analytical methods. Total lipid from plasma was extracted into chloroform/methanol (2:1) by the method of Folch et al. (27) Before the extraction, 30 μL of a 1mg/mL solution of diheptadecanoyl phosphatidylcholine and 30 μL of a 1 mg/mL solution of triheptadecanoyl glycerol (Nu-Check Prep, Elysian, N.Y.) in chloroform/methanol (1:1, vol/vol) were added as an internal standard to all samples. Plasma phospholipids and triglycerides were separated and transmethylated, and fatty acid methyl ester profiles were acquired by gas chromatography as described in Ref 2.

Interleukin-6 (IL-6) and tumor necrosis factor alpha (TNF-α) levels were determined using commercially available ELISA kits from R&D Systems (Minneapolis, Minn.) and Invitrogen (Camarillo, Calif.), respectively, according to the manufacturers' instructions. All samples were prepared and analyzed in duplicate.

Statistical Analyses. Results are presented as mean±SEM for each outcome (all fatty acid profiles and inflammatory markers). A generalized linear mixed model was used to assess the statistical significance of differences in mean outcome after adjusting for baseline levels among the different dietary groups over time (28). The covariance matrix of the parameter estimates was computed using a sandwich estimator, and further adjusted for small sample size by the method of Morel, Bokossa and Neerchal (29). Significance for all analysis was defined as $P \leq 0.05$. The type I error rate was controlled by limiting within-group comparisons to those specified a priori, and only when the diet-by-time interaction was significant. All analysis was performed with GraphPad Prism® v6, La Jolla, Calif. and SAS® v9, Cary, N.C.

Results

Food intake and body weight

There were no differences in food intake among the six groups for the duration of the study period. Average food intake per group remained consistent at approximately 3-4 g/mouse/day for 12 weeks. Animals in all dietary groups gained weight throughout the study. Baseline weights ranged from 23 to 24 g, and at the end of 12 weeks final weights ranged from 29 to 31 g (FIG. 1). No significant differences in weight were noted among the six groups. No animal demonstrated physical signs of essential fatty acid deficiency (EFAD), such as scaly dermatitis, hair loss, or skin atrophy.

Fatty acid profiles

Figure 2A:
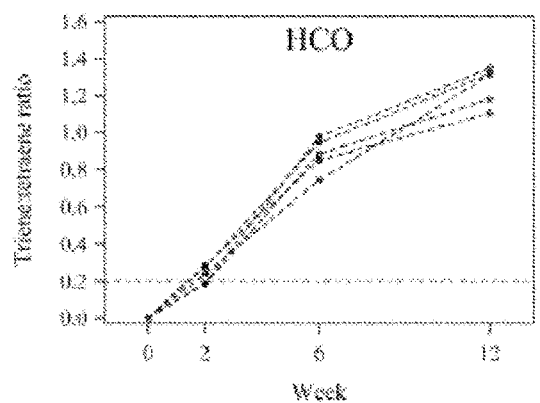
FIG. 2A-FIG. 2C are line graphs showing triene:tetraene ratio at weeks 0, 2, 6 and 12.
Figure 2B:
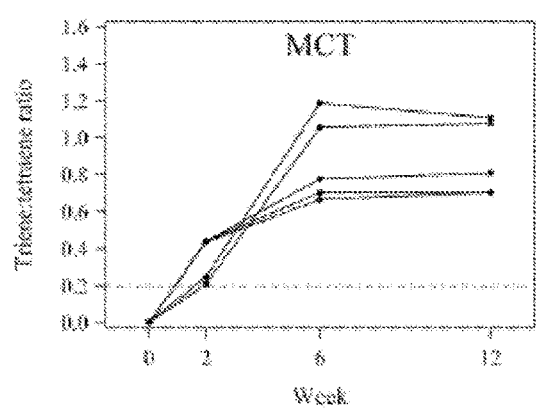
Figure 2C:
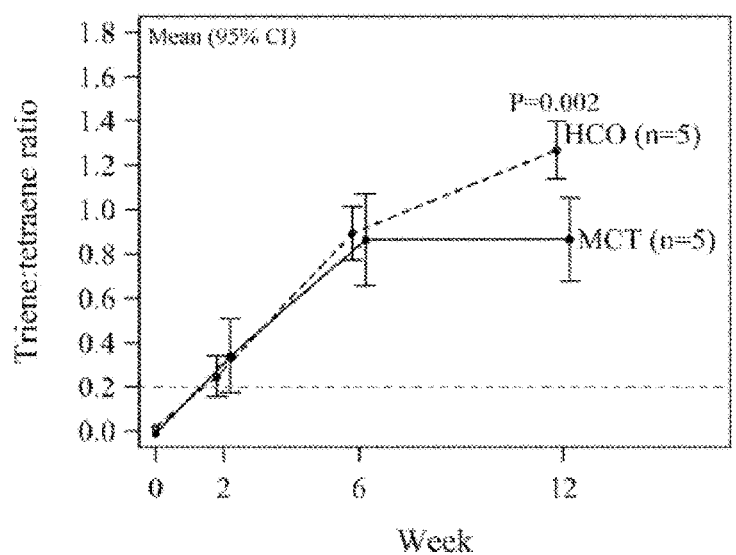

Animals in both MCT and HCO groups had biochemical EFAD, as defined by triene:tetraene ratios >0.2, by 2 weeks of dietary treatment, and these ratios continued to significantly increase for both groups over the remaining 10 weeks of treatment (HCO P<0.0001; MCT P=0.003). None of the groups fed diets containing PFO or SOY showed biochemical EFAD at any point. At 12 weeks, HCO-fed animals showed increased triene:tetraene ratios relative to MCT-fed animals (mean (95% CI) 0.40 (0.17, 0.63)) indicating a slightly greater degree of EFAD in the HCO group (FIG. 2A-FIG. 2C).

Figure 3A:
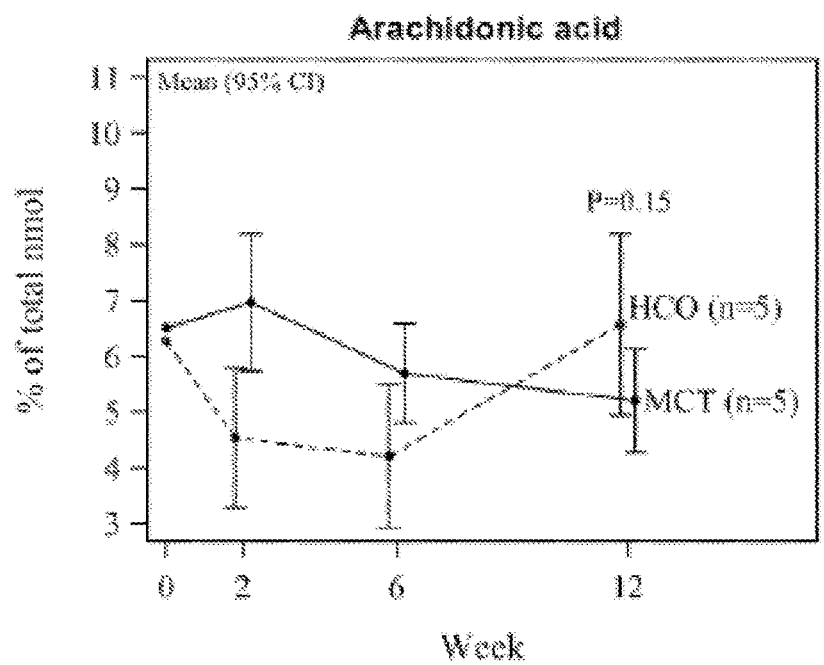
FIG. 3A-FIG. 3B are data graphs showing arachidonic acid over time (mean, 95% CI) (FIG. 3A) and mead acid at week 12 (median, IQR) (FIG. 3B). ARA is lower and mead acid is higher in the MCT group compared to the HCO group at 12 weeks.

The increased triene:tetraene ratio in HCO-fed animals is due to a higher mead acid (20:3n9) in the HCO group (FIG. 3B) despite a lower ARA in the MCT group compared to the HCO group at 12 weeks (5.21±0.45 and 6.57±0.78, respectively, P=0.15) (FIG. 3A). Without wishing to be bound by theory, this slight increase in mead acid can be attributable in part to the presence of substantial stearic acid (18:0), a mead acid precursor found in HCO and not in MCT oil.

Figure 4:
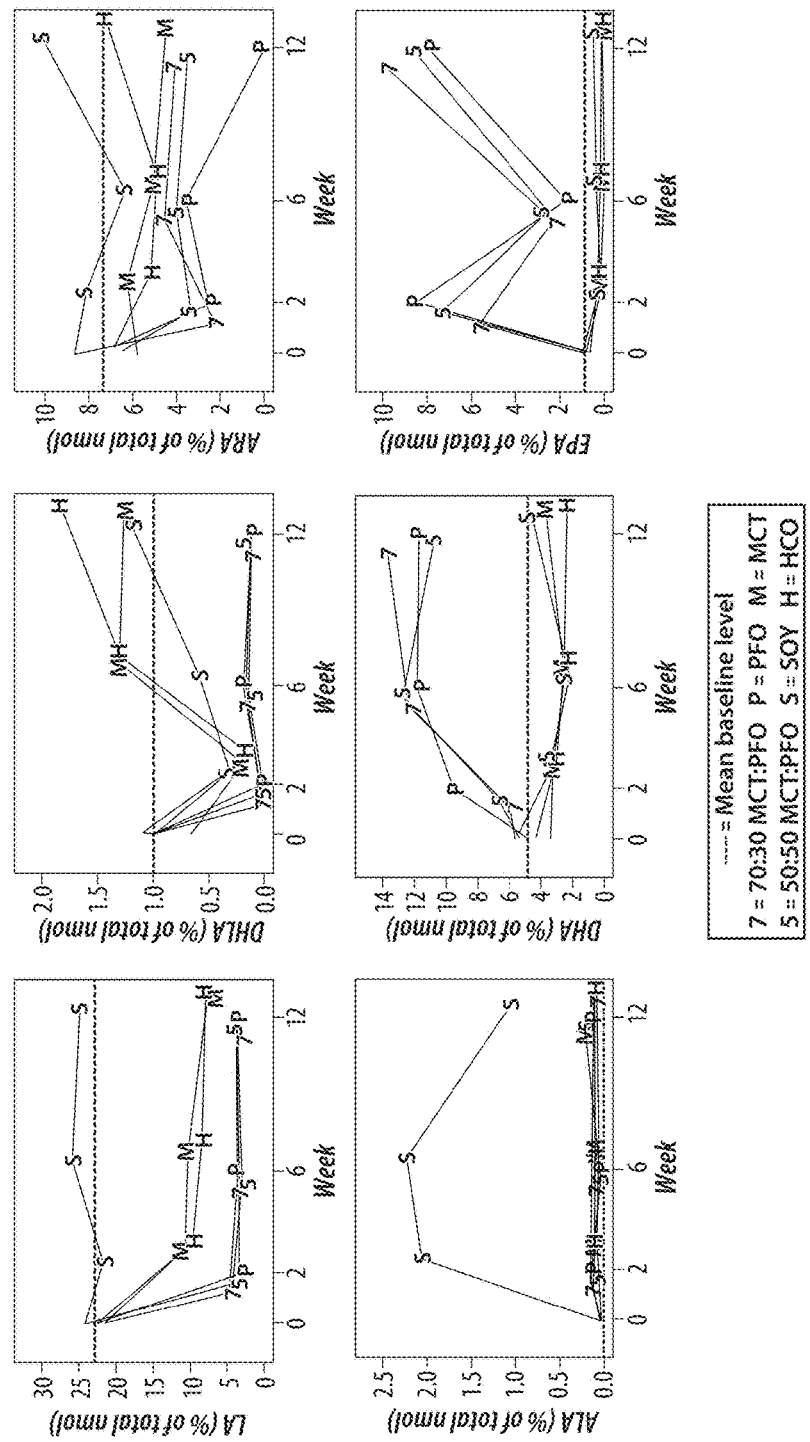
FIG. 4 is a set of data graphs showing omega-3 and omega-6 fatty acid concentrations. Shown are unadjusted means at weeks 0, 2, 6 and 12. The horizontal dashed reference line indicates the baseline mean. Data are shifted left or right of the week label to spread the data to enhance readability.

At 2 weeks of dietary treatment, significant differences among treatment groups were observed in plasma levels of various n-6 and n-3 fatty acids. SOY animals had only modest decreases in linoleic acid (LA, 18:2n6) from baseline (−2.4±2.9; P=0.40), compared to decreases on the order of 11% of total nmol in HCO and MCT groups (P<0.0001 for each), and even greater decreases on the order of 19% of total nmol in all groups containing PFO (P<0.0001 for each) (FIG. 4, top left panel). Dihomo-gamma-linolenic acid (20:3n6) was similar among SOY, HCO and MCT, and present in very low levels in all groups containing both MCT and PFO (FIG. 4, top middle panel). Arachidonic acid (ARA, 20:4n6) decreased by week 2 in all groups containing PFO (P<0.001), while unchanged from baseline for both SOY (P=0.81) and MCT (P=0.60). HCO experienced a modest decrease from baseline (P=0.04) (FIG. 4, top right panel). No significant changes were observed from baseline to week 2 for alpha linolenic acid (ALA, 18:3n3) (FIG. 4, bottom left panel). Docosahexaenoic acid (DHA, 22:6n3) increased by week 2 to 9.50±1.27% of total nmol in animals on the PFO diet (P=0.008) while remaining constant in all other groups (FIG. 4, bottom middle panel). Eicosapentaenoic acid (EPA, 20:5n3) increased in all groups containing PFO (P<0.05) while being barely detectable in the non-PFO containing groups (FIG. 4, bottom right panel).

Figure 3B:
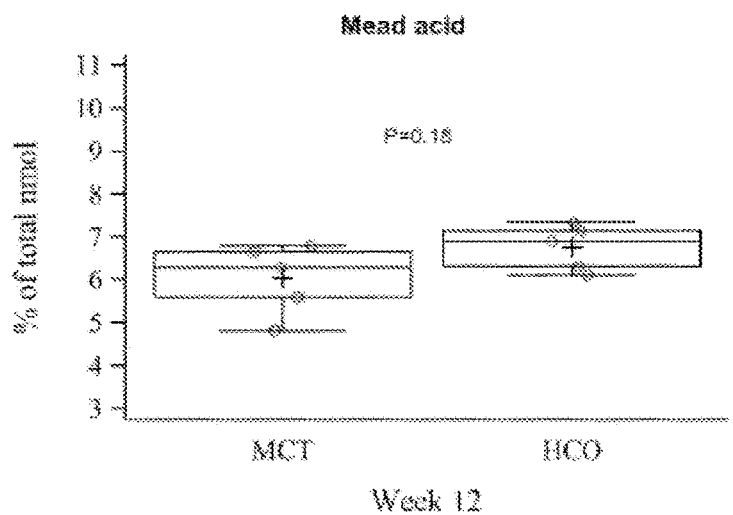

At 12 weeks, mice fed HCO and MCT still had detectable levels of LA, dihomo-gamma linolenic acid, and ARA, despite continued treatment with a diet deplete of these essential fatty acids. In fact, ARA levels in HCO and MCT groups were higher than in any PFO containing group. PFO, 50:50 MCT:PFO, and 70:30 MCT:PFO groups showed low levels of all n-6 fatty acids measured at 12 weeks. ARA was higher in SOY than all other groups at 12 weeks, significantly so when compared to the PFO groups (P<0.05). Although DHA and EPA were lower in all non-PFO containing groups, DHA levels were preserved in SOY and MCT, with only a modest decrease from baseline in HCO (−1.96±0.93; P=0.04), despite the lack of n-3 fatty acids in MCT and HCO and low n-3 source in SOY. FIG. 3A-FIG. 3B and FIG. 4 show n-3 and n-6 fatty acid levels, respectively.

IL-6 and TNF-α

Figure 5A:
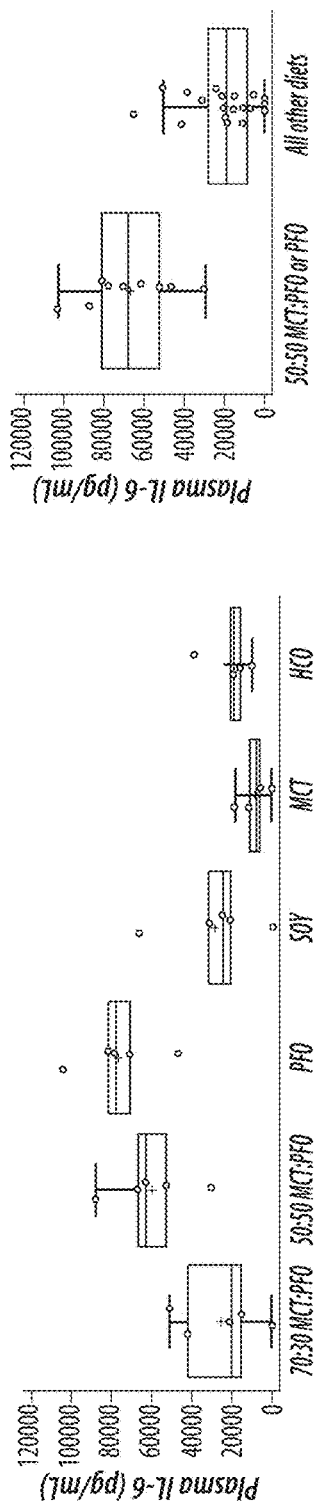
FIG. 5A-FIG. 5B are data graphs showing IL-6 and TNF-α, respectively, at week 12 from plasma of animals treated with different diet formulations. Diets 70:30 MCT:PFO, soy, MCT, and HCO are not different from one another (IL-6 P=0.30; TNF-α P=0.69). The 50:50 MCT:PFO and PFO diets are higher in both IL-6 and TNF-α than all other diets combined (P<0.0001 for each). Results are based on analysis of variance.
Figure 5B:
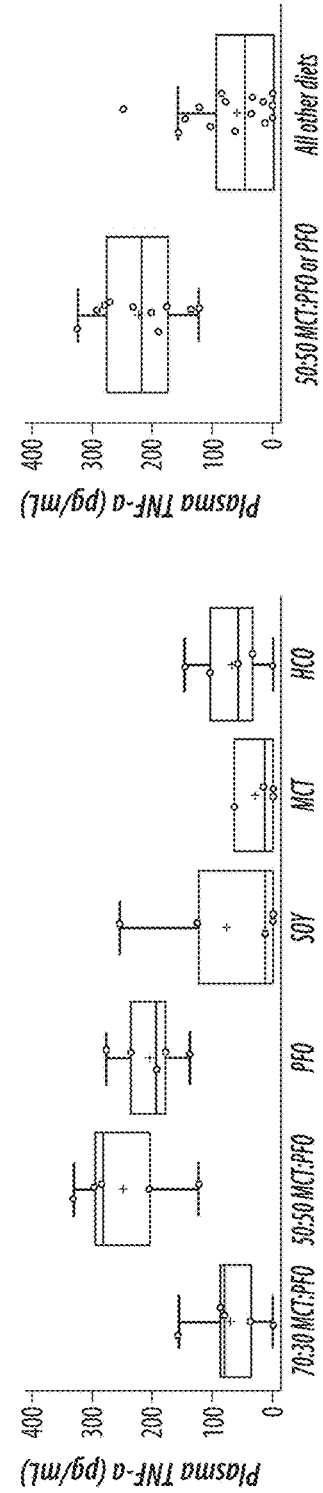

Measurement of IL-6 and TNF-α was performed on serum samples from all animals after 12 weeks of dietary treatment to establish a baseline. Baseline levels of IL-6 and TNF-α were found to be just at the detection threshold with no differences between dietary groups. After saline treatment, no differences were seen in either IL-6 or TNF-α from baseline in any dietary group (data not shown). After LPS treatment, IL-6 and TNF-α levels increased significantly in all groups. Animals fed PFO or 50:50 MCT:PFO diets were found to have the highest mean level of IL-6 when compared to all other dietary groups. Animals in the 50:50 MCT:PFO or PFO groups had highest levels of TNF-α relative to the other groups. IL-6 and TNF-α were lowest in MCT, though not significantly different than HCO, 70:30 MCT:PFO or SOY. FIG. 5A-FIG. 5B show the IL-6 and TNF-α levels, respectively, in all animals treated with LPS.

Liver analysis

Figure 6:
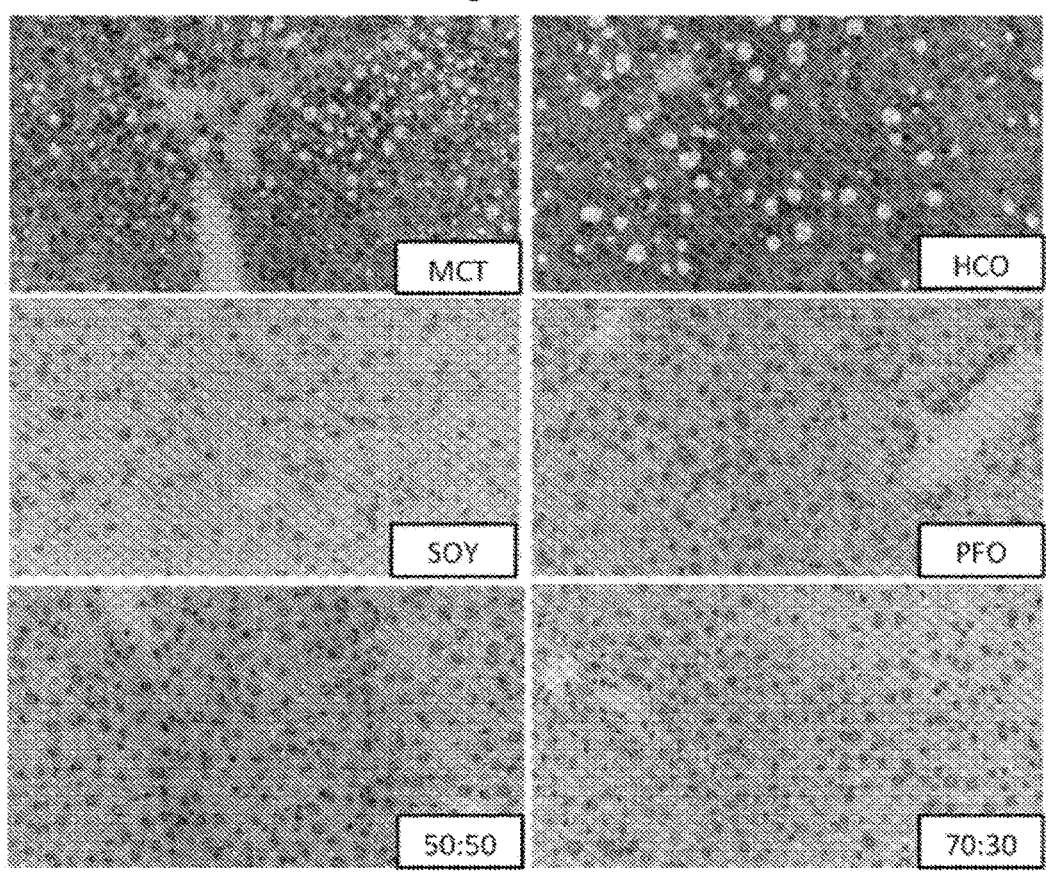
FIG. 6 is a set of histological images showing liver samples stained for Oil Red O. All MCT and HCO livers demonstrated significant peri-portal and mid-zonal micro- and macrosteatosis. SOY livers showed rare to mild mid-zonal microsteatosis. PFO, 50:50 MCT:PFO and 70:30 MCT:PFO livers appeared normal without evidence of hepatosteatosis.

All liver specimens from mice treated with different dietary compositions were stained for H&E and oil red O and analyzed. FIG. 6 shows a set of representative histological sections. All MCT and HCO livers showed significant peri-portal and mid-zonal micro- and macrosteatosis, representing the increased de novo lipogenesis of essential fatty acid deficiency. SOY livers showed rare to mild mid-zonal microsteatosis to a much lesser degree than MCT or HCO livers. PFO, 50:50 MCT:PFO and 70:30 MCT:PFO livers appeared grossly normal without evidence of hepatosteatosis. Among all groups, livers of animals treated with saline injection had glycogen deposits throughout the tissue, which were notably absent in livers of animals treated with LPS. Administration of LPS was not noted to have an effect on degree of steatosis or presence of inflammatory cells in any group.

Discussion

The incorporation of fish oil into parenteral nutrition (PN) formulations has been previously discussed to be an alternative approach to treat parenteral nutrition-associated liver injury. However, it has been speculated that fish oil monotherapy may be insufficient to support growth and prevent EFAD. Short-term animal studies have shown appropriate growth and prevention of EFAD after dietary treatment with native fish oil in mice when given as at least 20% of total calories, which supplies sufficient ARA to complement the very limited amount of linoleic acid found in fish oil (2). Nehra et al. demonstrated that animals fed a diet providing DHA and ARA as the sole source of fat in at a 20:1 ratio (similar to that which is generally found in native fish oil) at 2.1% of total calories is sufficient to sustain reproduction over several generations in mice (3). However, we are not aware of any study demonstrating that long-term dietary treatment with PFO alone (e.g., over 12 weeks) sustains growth and prevents EFAD in mice as shown in this Example.

As presented above, there was an increase in IL-6 and TNF-α following treatment with PFO-based diets and subsequent endotoxin challenge compared to HCO- and soy-based diets. This increased inflammatory response can be mitigated by the addition of MCT at ≥50% of fat calories. While Ling et al. (14) discussed that the addition of DHA and ARA to an HCO-based diet leads to increased IL-6 and C-reactive protein (CRP) after endotoxin administration, Ling et al. did not show mitigation of the increased inflammatory response by addition of MCT to a diet with DHA and ARA.

Presented herein is, in part, a surprising discovery that the inflammatory response can be mitigated by the addition of MCT to PFO. The increase in the systemic inflammatory response when using either PFO or only two of the active components (DHA and ARA) is unexpected given the multitude of evidence that standard fish oil preparations have been shown to be anti-inflammatory (e.g., 30,31). Previous reports have also shown a decrease in pro-inflammatory markers with fish oil treatment. For example, Endres et al. discussed that the production of IL-1 and TNF-α are decreased after endotoxin administration in healthy adults whose diet was supplemented with 18 g of fish oil for a period of six weeks (32). Previous studies have often utilized native fish oil as a supplement in much smaller amounts than studied by Endres et al. and that the supplements are taken with a normal diet containing substantial amounts of other fats (32-34). Thus, it would not be obvious to add MCT to fish oil for mitigating an unexpected increase in systemic inflammatory response due to administration of either PFO or DHA and ARA.

In native or unpurified fish oil, EPA and DHA are generally present at 25-30% of total fatty acids and ARA at approximately 0.5-1% with the remaining majority of fatty acids as saturated fatty acids (35). Without wishing to be bound by theory, it is thought that the difference in inflammatory potential seen in the present Example and previous reports is related to the principal fatty acids that underlie inflammation. ARA is presumed to be pro-inflammatory through its production of 2-series eicosanoids like prostaglandin and prostacyclin and 4 series leukotrienes (15, 36). In contrast, EPA and DHA are anti-inflammatory in part due to the production of 3-series prostanoids and 5-series leukotrienes, and DHLA is previously discussed to be anti-inflammatory from its production of 1-series prostanoids (37).

In the mice study shown in the present Example, while ARA levels are high and EPA levels low in the SOY group, DHLA levels are also higher in PFO-containing groups compared to those not containing PFO. Moreover, a state of essential fatty acid deficiency in itself, as with HCO and MCT, has been shown to lead to increased mortality in humans due to infection, presumably because of the underlying decreased response to endotoxin challenge (38). In contrast, groups containing PFO have the highest EPA and DHA and lowest ARA, which should result in down-regulated inflammation; notably, these groups have essentially no DHLA. Yet the mice with a PFO-based diet unexpectedly showed an increase in the systemic inflammatory response to endotoxin challenge. Whether the effect of DHLA would be enough to change the degree of inflammation vis-à-vis PFO or whether EPA and DHA alone in these amounts might have opposite effects are not known. Furthermore the increase in systemic inflammatory response also reflects an increased immune response, which, under certain circumstances, could be beneficial as in the correction of essential fatty acid deficiency. Nevertheless, the results presented herein should provide guidance on the potential effects of purifying fish oil and the potential fatty acid interactions that this might entail. The results generated from these experiments show that a diet produced from dilution of PFO by at least 50% MCT results in optimal liver histology and a more beneficial (reduced) inflammatory profile in response to endotoxin challenge. This diet also provides fat calories in an amount that allows the reduction of the carbohydrate burden.

The results presented in this Example indicate that long-term nutrition with PFO as the sole source of fat calories will sustain growth and prevent EFAD. Further, the addition of MCT to the PFO formulation decreases the recipient's inflammatory response when challenged. Thus, the inclusion of MCT in very long chain fatty acid lipid emulsions given as PN formulations is therapeutically useful for subjects with disease states resulting from chronic inflammation, or individuals at risk for inflammatory challenge.

REFERENCES

The cited references and publications in the specification and Examples section are incorporated herein by reference in their entirety.

1. Le H D, Meisel J A, de Meijer V E, Gura K M, Puder M. The essentiality of arachidonic acid and docosahexaenoic acid. Prostaglandins, leukotrienes, and essential fatty acids. August-September 2009; 81(2-3):165-170.
2. Ling P R, Puder M, Bistrian B R. Purified fish oil eliminating linoleic and alpha linolenic acid meets essential fatty acid requirements in rats. Metabolism: clinical and experimental. October 2012; 61(10):1443-1451.
3. Nehra D, Le H D, Fallon E M, et al. Prolonging the female reproductive lifespan and improving egg quality with dietary omega-3 fatty acids. Aging cell. December 2012; 11(6):1046-1054.
4. Colomb V, Jobert-Giraud A, Lacaille F, Goulet O, Fournet J C, Ricour C. Role of lipid emulsions in cholestasis associated with long-term parenteral nutrition in children. JPEN. Journal of parenteral and enteral nutrition. November-December 2000; 24(6):345-350.
5. Kurvinen A, Nissinen M J, Andersson S, et al. Parenteral plant sterols and intestinal failure-associated liver disease in neonates. Journal of pediatric gastroenterology and nutrition. June 2012; 54(6):803-811.
6. Merritt R J. Cholestasis associated with total parenteral nutrition. Journal of pediatric gastroenterology and nutrition. January 1986; 5(1):9-22.
7. Squires R H, Duggan C, Teitelbaum D H, et al. Natural history of pediatric intestinal failure: initial report from the Pediatric Intestinal Failure Consortium. The Journal of pediatrics. October 2012; 161(4):723-728 e722.
8. Calkins K L, Dunn J C, Shew S B, et al. Pediatric Intestinal Failure-Associated Liver Disease Is Reversed With 6 Months of Intravenous Fish Oil. JPEN. Journal of parenteral and enteral nutrition. Jul. 26, 2013.
9. Premkumar M H, Carter B A, Hawthorne K M, King K, Abrams S A. High rates of resolution of cholestasis in parenteral nutrition-associated liver disease with fish oil-based lipid emulsion monotherapy. The Journal of pediatrics. April 2013; 162(4):793-798 e791.
10. Puder M, Valim C, Meisel J A, et al. Parenteral fish oil improves outcomes in patients with parenteral nutrition-associated liver injury. Annals of surgery. September 2009; 250(3):395-402.
11. Guglielmi F W, Regano N, Mazzuoli S, et al. Catheter-related complications in long-term home parenteral nutrition patients with chronic intestinal failure. The journal of vascular access. October-December 2012; 13(4):490-497.
12. Pironi L, Joly F, Forbes A, et al. Long-term follow-up of patients on home parenteral nutrition in Europe: implications for intestinal transplantation. Gut. January 2011; 60(1):17-25.
13. Sanders R A, Sheldon G F. Septic complications of total parenteral nutrition. A five year experience. American journal of surgery. August 1976; 132(2):214-220.
14. Ling P R, Malkan A, Le H D, Puder M, Bistrian B R. Arachidonic acid and docosahexaenoic acid supplemented to an essential fatty acid-deficient diet alters the response to endotoxin in rats. Metabolism: clinical and experimental. March 2012; 61(3):395-406.
15. Cook J A, Wise W C, Halushka P V. Elevated thromboxane levels in the rat during endotoxic shock: protective effects of imidazole, 13-azaprostanoic acid, or essential fatty acid deficiency. The Journal of clinical investigation. January 1980; 65(1):227-230.
16. Kono H, Enomoto N, Connor H D, et al. Medium-chain triglycerides inhibit free radical formation and TNF-alpha production in rats given enteral ethanol. American journal of physiology. Gastrointestinal and liver physiology. March 2000; 278(3):G467-476.
17. Nanji A A, Jokelainen K, Tipoe G L, Rahemtulla A, Dannenberg A J. Dietary saturated fatty acids reverse inflammatory and fibrotic changes in rat liver despite continued ethanol administration. The Journal of pharmacology and experimental therapeutics. November 2001; 299(2):638-644.
18. Ronis M J, Korourian S, Zipperman M, Hakkak R, Badger T M. Dietary saturated fat reduces alcoholic hepatotoxicity in rats by altering fatty acid metabolism and membrane composition. The Journal of nutrition. April 2004; 134(4):904-912.
19. Kono H, Fujii H, Asakawa M, et al. Medium-chain triglycerides enhance secretory IgA expression in rat intestine after administration of endotoxin. American journal of physiology. Gastrointestinal and liver physiology. June 2004; 286(6):G1081-1089.
20. Kono H, Fujii H, Asakawa M, et al. Protective effects of medium-chain triglycerides on the liver and gut in rats administered endotoxin. Annals of surgery. February 2003; 237(2):246-255.
21. Vanek V W, Seidner D L, Allen P, et al. A.S.P.E.N. position paper: Clinical role for alternative intravenous fat emulsions. Nutrition in clinical practice: official publication of the American Society for Parenteral and Enteral Nutrition. April 2012; 27(2):150-192.
22. Le H D, Meisel J A, de Meijer V E, et al. Docosahexaenoic acid and arachidonic acid prevent essential fatty acid deficiency and hepatic steatosis. JPEN. Journal of parenteral and enteral nutrition. July 2012; 36(4):431-441.
23. Le H D, de Meijer V E, Zurakowski D, Meisel J A, Gura K M, Puder M. Parenteral fish oil as monotherapy improves lipid profiles in children with parenteral nutrition-associated liver disease. JPEN. Journal of parenteral and enteral nutrition. September-October 2010; 34(5):477-484.
24. Nehra D, Fallon E M, Potemkin A K, et al. A Comparison of 2 Intravenous Lipid Emulsions: Interim Analysis of a Randomized Controlled Trial. JPEN. Journal of parenteral and enteral nutrition. Jun. 14, 2013.
25. Lillie R D. Histopathologic Technic and Practical Histochemistry. 3rd ed. New York: McGraw-Hill Book Co.; 1965.
26. Bancroft J D, Gamble M. Theory and Practice of Histological Techniques. Edinburgh: Churchill Livingston; 2007.
27. Folch J, Lees M, Sloane Stanley G H. A simple method for the isolation and purification of total lipides from animal tissues. The Journal of biological chemistry. May 1957; 226(1):497-509.
28. Liang K Y, Zeger S L. Longitudinal data analysis using generalized linear models. Biometrika. 1986; 73:13-22.
29. Morel J, Bokossa M, Neerchal N. Small sample correction for the variance of GEE estimators. Biometrical Journal. 2003; 4:395-409.
30. Mascioli E, Leader L, Flores E, Trimbo S, Bistrian B, Blackburn G. Enhanced survival to endotoxin in guinea pigs fed IV fish oil emulsion. Lipids. June 1988; 23(6):623-625.
31. Pomposelli J J, Mascioli E A, Bistrian B R, Lopes S M, Blackburn G L. Attenuation of the febrile response in guinea pigs by fish oil enriched diets. JPEN. Journal of parenteral and enteral nutrition. March-April 1989; 13(2):136-140.
32. Endres S, Ghorbani R, Kelley V E, et al. The effect of dietary supplementation with n-3 polyunsaturated fatty acids on the synthesis of interleukin-1 and tumor necrosis factor by mononuclear cells. The New England journal of medicine. Feb. 2, 1989; 320(5):265-271.
33. Murphy K J, Galvin K, Kiely M, Morrissey P A, Mann N J, Sinclair A J. Low dose supplementation with two different marine oils does not reduce pro-inflammatory eicosanoids and cytokines in vivo. Asia Pacific journal of clinical nutrition. 2006; 15(3):418-424.
34. Zulyniak M A, Perreault M, Gerling C, Spriet L L, Mutch D M. Fish oil supplementation alters circulating eicosanoid concentrations in young healthy men. Metabolism: clinical and experimental. August 2013; 62(8):1107-1113.
35. Sierra P, Ling P R, Istfan N W, Bistrian B R. Fish oil feeding improves muscle glucose uptake in tumor necrosis factor-treated rats. Metabolism: clinical and experimental. October 1995; 44(10):1365-1370.
36. Ling P R, Boyce P, Bistrian B R. Role of arachidonic acid in the regulation of the inflammatory response in TNF-alpha-treated rats. JPEN. Journal of parenteral and enteral nutrition. September-October 1998; 22(5):268-275.
37. Palombo J D, DeMichele S J, Boyce P J, et al. Effect of short-term enteral feeding with eicosapentaenoic and gamma-linolenic acids on alveolar macrophage eicosanoid synthesis and bactericidal function in rats. Critical care medicine. September 1999; 27(9):1908-1915.
38. Hansen A, Wiese H, Boelsche A, Haggard M, Adam D, Davis H. Role of linoleic acid in infant nutrition. Pediatrics. 1963; 31(suppl):171-192.

The invention claimed is:
1. An emulsion formulation for total enteral or parenteral nutrition of a human subject comprising as the sole fat components:
   (i) medium chain triglycerides; and
   (ii) very long chain fatty acids selected from the group consisting of (a) very long chain omega-3 polyunsaturated fatty acids (VLC omega-3 PUFAs) and (b) docosahexaenoic acid (DHA) and arachidonic acid (AA) in a ratio of about 10:1 (v/v or w/w) to about 2000:1 (v/v or w/w);
   wherein the weight ratio of the medium chain triglycerides and VLC omega-3 PUFAs is greater than 1:1;
   wherein the sole fat components provide about 10% to about 90% total calories of the formulation, and
   wherein the medium chain triglycerides provide about 25%-95% total fat calories.
2. The emulsion formulation of claim 1, wherein the sole fat components are present in an amount of about 10 g to about 50 g per 100 mL of the formulation.
3. The emulsion formulation of claim 2, wherein the sole fat components are present in an amount of about 20 g to about 30 g per 100 mL of the formulation.
4. The emulsion formulation of claim 2, wherein the total calories of the formulation is from about 1000 kcal/kg of the formulation to about 4000 kcal/kg of the formulation.
5. The emulsion formulation of claim 1, wherein the weight ratio of the medium chain triglycerides to the very long chain fatty acids is about 70:30.
6. The emulsion formulation of claim 1, wherein the medium chain triglycerides have a carbon length of 6, 8, and/or 10.
7. The emulsion formulation of claim 1, wherein the very long chain fatty acids provide about 2-10% total calories of the formulation.
8. The emulsion formulation of claim 1, wherein the very long chain fatty acids provide about 3% total calories of the formulation.
9. The emulsion formulation of claim 1, wherein the VLC omega-3 PUFAs are selected from the group consisting of docosahexaenoic acid (DHA), eicosapentaenoic acid (EPA), and 5-docosapentaenoic acid (DPA), and combinations thereof.

10. The emulsion formulation of claim 1, wherein the very long chain fatty acids are docosahexaenoic acid (DHA) and arachidonic acid (AA) in a ratio of about 20:1 (v/v or w/w).

11. The emulsion formulation of claim 1, wherein:
a) the sole fat components are present in an amount of about 40 g/100 ml;
b) the medium chain triglycerides have a carbon length of 6, 8, and/or 10, and provided at a weight ratio of 70:30 to the weight of the very long chain fatty acids;
c) wherein the very long chain fatty acids are docosahexaenoic acid (DHA) and arachidonic acid (AA) present in a ratio of about 20:1 (v/v or w/w) wherein these very long chain fatty acids provide about 3% total calories of the formulation;
d) wherein the total calories of the formulation is from about 1000 kcal/kg to about 4000 kcal/kg;
e) wherein the above total fat components provide from about 10% to about 90% total calories of the formulation; and
f) wherein the medium chain triglycerides provide from about 25%-95% total fat calories.

12. The emulsion formulation of claim 1, wherein the very long chain fatty acids provide about 0.05-70% total calories of the formulation.

\* \* \* \* \*